United States Patent
Rondeau

(10) Patent No.: US 7,198,652 B2
(45) Date of Patent: Apr. 3, 2007

(54) COMPOSITION FOR DYEING KERATINOUS FIBERS WITH A CATIONIC DIRECT DYE AND A QUATERNARY AMMONIUM SALT

(75) Inventor: Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/384,520

(22) Filed: Mar. 21, 2006

(65) Prior Publication Data

US 2006/0156487 A1    Jul. 20, 2006

Related U.S. Application Data

(63) Continuation of application No. 10/880,615, filed on Jul. 1, 2004, which is a continuation of application No. 09/529,835, filed as application No. PCT/FR99/01865 on Jul. 28, 1999, now abandoned.

(30) Foreign Application Priority Data

Aug. 19, 1998    (FR) .................. 98 10547

(51) Int. Cl.
*A61K 7/13*    (2006.01)

(52) U.S. Cl. ............... 8/405; 8/406; 8/437; 8/570; 8/571; 8/573; 8/575; 8/606; 8/638; 8/644; 8/654; 8/677

(58) Field of Classification Search ............. 8/405, 8/406, 437, 570, 571, 573, 575, 606, 638, 8/644, 654, 677
See application file for complete search history.

(56) References Cited

U.S. PATENT DOCUMENTS

| | | | |
|---|---|---|---|
| 3,869,454 A | 3/1975 | Lang et al. | |
| 3,955,918 A | 5/1976 | Lang | |
| 3,985,499 A | 10/1976 | Lang et al. | |
| 4,025,301 A | 5/1977 | Lang | |
| 4,168,144 A | 9/1979 | Curry et al. | |
| 4,823,985 A | 4/1989 | Grollier et al. | |
| 5,376,146 A * | 12/1994 | Casperson et al. | 8/408 |
| 5,711,765 A * | 1/1998 | Audousset | 8/426 |
| 5,993,490 A | 11/1999 | Rondeau et al. | |
| 6,001,135 A * | 12/1999 | Rondeau et al. | 8/407 |
| 6,039,936 A * | 3/2000 | Restle et al. | 424/70.1 |

FOREIGN PATENT DOCUMENTS

| | | |
|---|---|---|
| EP | 0 312 343 | 4/1989 |
| EP | 0 705 597 | 4/1996 |
| EP | 0 819 422 | 1/1998 |
| EP | 0 850 637 | 7/1998 |
| EP | 0 850 638 | 7/1998 |
| FR | 2 140 205 | 1/1973 |
| FR | 2 189 006 | 1/1974 |
| FR | 2 282 860 | 3/1976 |
| FR | 2 285 851 | 4/1976 |
| FR | 2 586 913 | 3/1997 |
| JP | 10182379 A * | 7/1998 |
| WO | WO 95/01772 | 1/1995 |
| WO | WO 95/15144 | 6/1995 |
| WO | WO 97/19998 * | 6/1997 |
| WO | WO 99/20234 | 4/1999 |
| WO | WO 99/20235 | 4/1999 |

* cited by examiner

*Primary Examiner*—Eisa Elhilo
(74) *Attorney, Agent, or Firm*—Finnegan, Henderson, Farabow, Garrett & Dunner L.L.P.

(57) ABSTRACT

The invention relates to a composition for dyeing keratinous fibers, in particular human keratinous fibers such as hair, comprising, in an appropriate dyeing medium, at least one cationic direct dye of a given formula, and which is characterized in that it contains, in addition, at least one quaternary ammonium salt.

The invention also relates to the dyeing methods and devices using it.

43 Claims, No Drawings

COMPOSITION FOR DYEING KERATINOUS FIBERS WITH A CATIONIC DIRECT DYE AND A QUATERNARY AMMONIUM SALT

This application is a continuation of U.S. patent application Ser. No. 10/880,615, filed Jul. 1, 2004 now allowed, which is a continuation of U.S. patent application Ser. No. 09/529,835, filed May 9, 2000, now abandoned, which is a national stage application of PCT/FR99/01865, filed Jul. 28, 1999, which claims the benefit of French Application No. 98/10547, filed Aug. 19, 1998, all of which are incorporated herein by reference.

The invention relates to a composition for dyeing keratinous fibres, in particular human keratinous fibres such as hair, comprising, in an appropriate dyeing medium, at least one cationic direct dye of a given formula, and at least one quaternary ammonium salt.

The subject of the invention is also the dyeing methods and devices using the said composition.

In the hair domain, it is possible to distinguish two types of dyeing.

The first is the semipermanent or temporary dyeing, or direct dyeing, which involves dyes capable of bringing the natural colour of the hair a more or less marked colour modification which is resistant, where appropriate, to several shampooings. These dyes are called direct dyes; they can be used with or without oxidizing agent. In the presence of oxidizing agent, the aim is to obtain a lightening dyeing. Lightening dyeing is performed by applying to the hair the fresh mixture of a direct dye and of an oxidizing agent and makes it possible in particular to obtain, by lightening of the melanin of the hair, an advantageous effect such as a uniform colour in the case of grey hair or to make the colour stand out in the case of naturally pigmented hair.

The second is permanent dyeing or oxidation dyeing. The latter is performed with so-called "oxidation" dyes comprising oxidation dye precursors and couplers. The oxidation dye precursors, commonly called "oxidation bases" are compounds which are initially colourless or faintly coloured which develop their dyeing power inside the hair in the presence of oxidizing agents added at the time of use, leading to the formation of coloured and dyeing compounds. The formation of these coloured and dyeing compounds results either from an oxidative condensation of the "oxidation bases" with themselves, or an oxidative condensation of the "oxidation bases" with colour modifying compounds commonly called "couplers" and generally present in the dyeing compositions used in oxidation dyeing.

To vary the shades obtained with the said oxidation dyes, or to increase their shimmer, direct dyes are sometimes added to them.

Among the cationic direct dyes available in the field of dyeing of keratinous fibres, especially human keratinous fibres, compounds are already known whose structure is developed in the text which follows; nevertheless, these dyes lead to colours which exhibit characteristics which are still inadequate from the point of view of the intensity and homogeneity of the colour distributed along the fibre; it is said, in this case, that the colour is too selective, and from the point of view of fastness, in terms of resistance to various attacks to which the hair may be subjected (light, adverse weather conditions, shampooings).

However, after major research studies carried out on this question, the applicant has just now discovered that it is possible to obtain novel compositions for dyeing keratinous fibres which are capable of giving intense and only slightly selective colours which are quite resistant nevertheless to the various attacks to which the hair may be subjected, by combining at least one particular anionic surfactant with at least one cationic direct dye known in the prior art and which have the respective formulae defined hereinafter.

This discovery forms the basis of the present invention.

The first subject of the present invention is therefore a composition for dyeing keratinous fibres and in particular human keratinous fibres such as hair, containing in an appropriate dyeing medium, (i) at least one cationic direct dye whose structure corresponds to the formulae (I) to (IV) defined hereinafter, characterized in that it contains in addition (ii) at least one quaternary ammonium salt.

(i) The cationic direct dye which can be used according to the present invention is a compound chosen from those of the following formulae (I), (II), (III), (III'), (IV):

a) the compounds of the following formula (I):

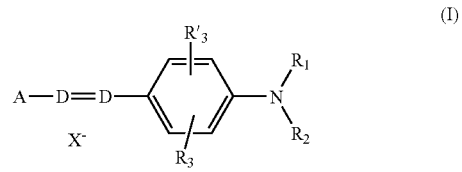

in which:

D represents a nitrogen atom or the —CH group, $R_1$ and $R_2$, which are identical or different, represent a hydrogen atom; a $C_1$–$C_4$ alkyl radical which may be substituted with a —CN, —OH or —NH$_2$ radical or form with a carbon atom of the benzene ring an optionally oxygen-containing or nitrogen-containing heterocycle which may be substituted with one or more $C_1$–$C_4$ alkyl radicals; a 4'-aminophenyl radical, $R_3$ and $R'_3$, which are identical or different, represent a hydrogen or halogen atom chosen from chlorine, bromine, iodine and fluorine, a cyano, $C_1$–$C_4$ alkyl, $C_1$–$C_4$ alkoxy or acetyloxy radical, $X^-$ represents an anion which is preferably chosen from chloride, methylsulphate and acetate, A represents a group chosen from the following structures $A_1$ to $A_{19}$:

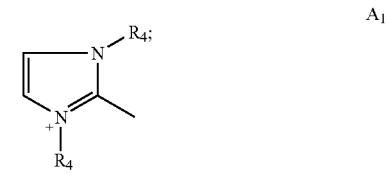

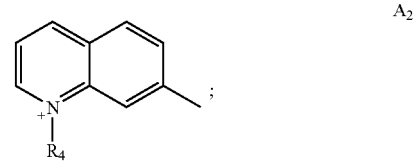

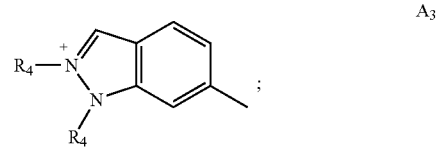

A₄ 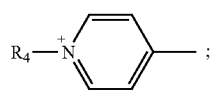

A₅ 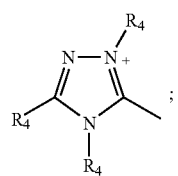

A₆ 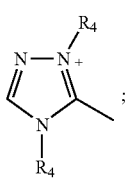

A₇ 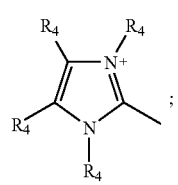

A₈ 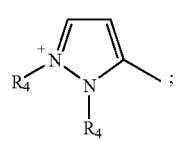

A₉ 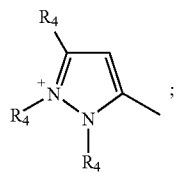

A₁₀ 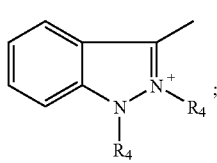

A₁₁ 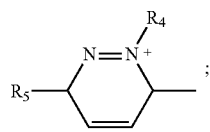

A₁₂ 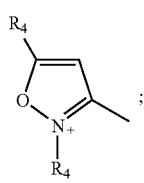

A₁₃ 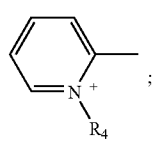

A₁₄ 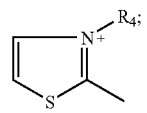

A₁₅ 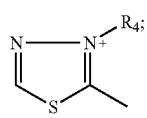

A₁₆ 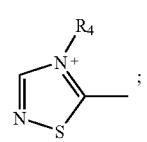

A₁₇ 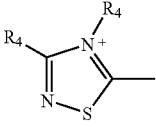

A₁₈ 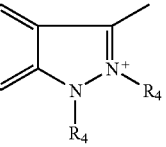 and

A₁₉ 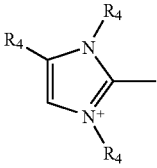

in which $R_4$ represents a $C_1$–$C_4$ alkyl radical which may be substituted with a hydroxyl radical and $R_5$ represents a $C_1$–$C_4$ alkoxy radical, with the proviso that when D represents —CH, A represents $A_4$ or $A_{13}$ and $R_3$ is different from an alkoxy radical, then $R_1$ and $R_2$ do not simultaneously denote a hydrogen atom;

b) the compounds of the following formula (II):

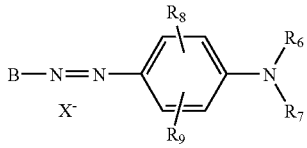

(II)

in which:

$R_6$ represents a hydrogen atom or a $C_1$–$C_4$ alkyl radical, $R_7$ represents a hydrogen atom, an alkyl radical which may be substituted with a —CN radical or with an amino group, a 4'-aminophenyl radical or forms with $R_6$ an optionally oxygen-containing and/or nitrogen-containing heterocycle which may be substituted with a $C_2$–$C_4$ alkyl radical, $R_8$ and $R_9$, which are identical or different, represent a hydrogen atom, a halogen atom such as bromine, chlorine, iodine or fluorine, a $C_1$–$C_4$ alkyl or $C_1$–$C_4$ alkoxy radical, a —CN radical, X⁻ represents an anion which is preferably chosen from chloride, methylsulphate and acetate, B represents a group chosen from the following structures B1 to B6:

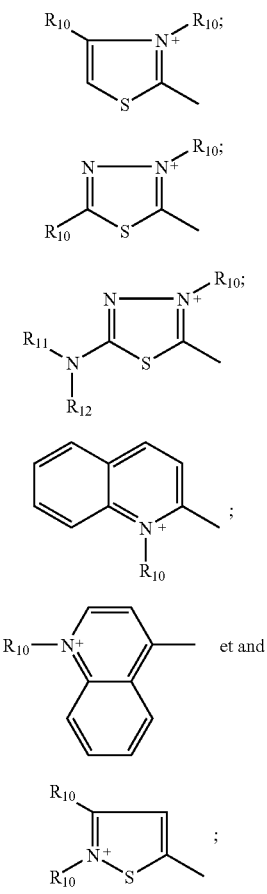

in which $R_{10}$ represents a $C_1$–$C_4$ alkyl radical, $R_{11}$ and $R_{12}$, which are identical or different, represent a hydrogen atom or a $C_1$–$C_4$ alkyl radical;

c) the compounds of the following formulae (III) and (III'):

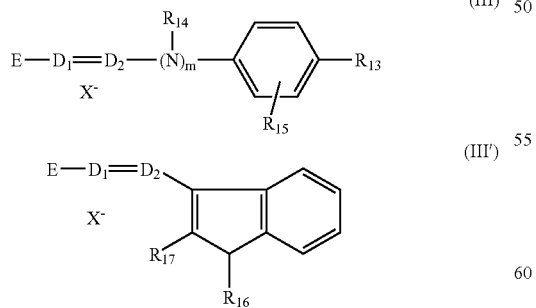

in which:

$R_{13}$ represents a hydrogen atom, a $C_1$–$C_4$ alkoxy radical, a halogen atom such as bromine, chlorine, iodine or fluorine or an amino radical, $R_{14}$ represents a hydrogen atom, a $C_1$–$C_4$ alkyl radical or forms with a carbon atom of the benzene ring a heterocycle which is optionally oxygen-containing and/or substituted with one or more $C_1$–$C_4$ alkyl groups, $R_{15}$ represents a hydrogen or halogen atom such as bromine, chlorine, iodine of fluorine, $R_{16}$ and $R_{17}$, which are identical or different, represent a hydrogen atom or a $C_1$–$C_4$ alkyl radical, $D_1$ and $D_2$, which are identical or different, represent a nitrogen atom or the —CH group, m=0 or 1, it being understood that when $R_{13}$ represents an unsubstituted amino group, then $D_1$ and $D_2$ simultaneously represent a —CH group and m=0, X⁻ represents an anion which is preferably chosen from chloride, methylsulphate and acetate, E represents a group chosen from the following structures E1 to E8:

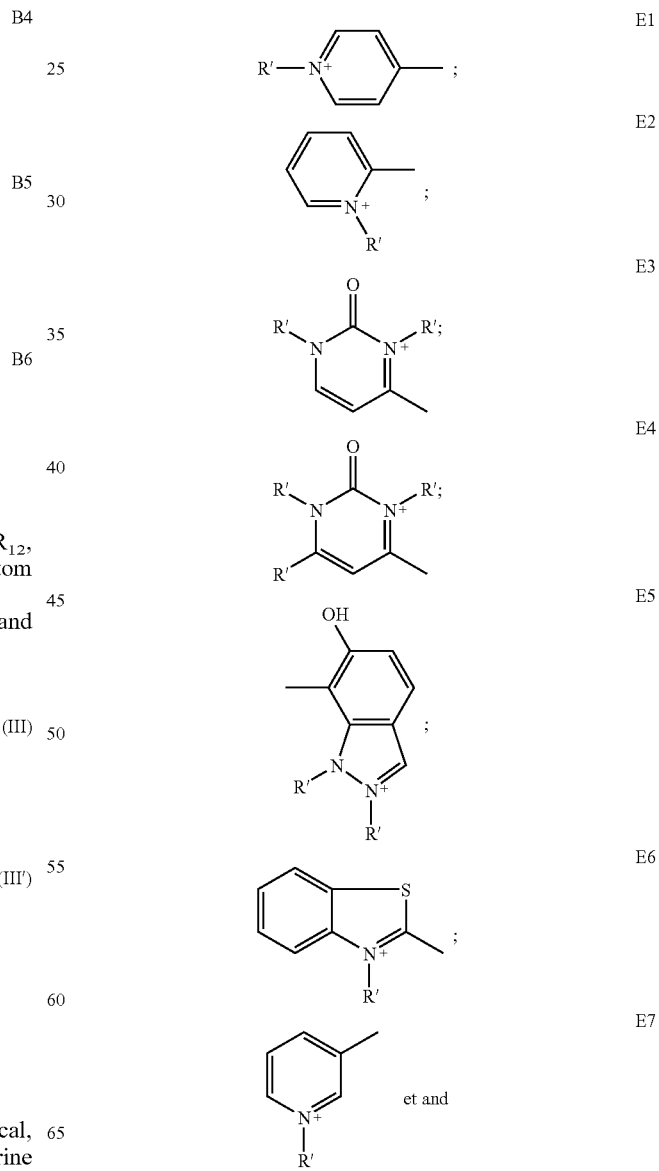

-continued

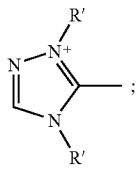
E8 in which R' represents a $C_1$–$C_4$ alkyl radical;

when m=0 and $D_1$ represents a nitrogen atom, then E may also denote a group having the following structure E9:

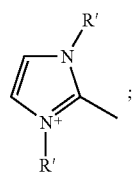
E9 in which R' represents a $C_1$–$C_4$ alkyl radical, d) the compounds of the following formula (IV):

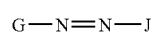
(IV)

in which:

the symbol G represents a group chosen from the following structures $G_1$ to $G_3$:

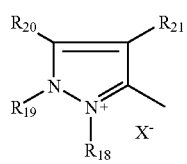
$G_1$

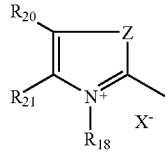
$G_2$

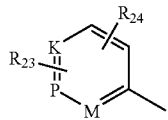
$G_3$ in which structures $G_1$ to $G_3$, $R_{18}$ denotes a $C_1$–$C_4$ alkyl radical, a phenyl radical which may be substituted with a $C_1$–$C_4$ alkyl radical or a halogen atom chosen from chlorine, bromine, iodine and fluorine;

$R_{19}$ denotes a $C_1$–$C_4$ alkyl radical or a phenyl radical;

$R_{20}$ and $R_{21}$, which are identical or different, represent a $C_1$–$C_4$ alkyl radical, a phenyl radical, or form together in $G_1$ a benzene ring which is substituted with one or more $C_1$–$C_4$ alkyl, $C_1$–$C_4$ alkoxy or $NO_2$ radicals, or form together in $G_2$ a benzene ring which is optionally substituted with one or more $C_1$–$C_4$ alkyl, $C_1$–$C_4$ alkoxy or $NO_2$ radicals;

$R_{20}$ may denote, in addition, a hydrogen atom;

Z denotes an oxygen or sulphur atom or an —$NR_{19}$ group;

M represents a group —CH, —CR (R denoting $C_1$–$C_4$ alkyl), or —$NR_{22}(X^-)_r$;

K represents a group —CH, —CR (R denoting $C_1$–$C_4$ alkyl), or —$NR_{22}(X^-)_r$;

P represents a group —CH, —CR (R denoting $C_1$–$C_4$ alkyl), or —$NR_{22}(X^-)_r$; r denotes zero or 1;

$R_{22}$ represents an $O^-$ atom, a $C_1$–$C_4$ alkoxy radical or a $C_1$–$C_4$ alkyl radical;

$R_{23}$ and $R_{24}$, which are identical or different, represent a hydrogen or halogen atom chosen from chlorine, bromine, iodine and fluorine, a $C_1$–$C_4$ alkyl radical, a $C_1$–$C_4$ alkoxy radical or an —$NO_2$ radical;

$X^-$ represents an anion which is preferably chosen from chloride, iodide, methylsulphate, ethylsulphate, acetate and perchlorate;

with the proviso that if $R_{22}$ denotes $O^-$, then r denotes zero;

if K or P or M denote —N—$(C_1$–$C_4$ alkyl)$X^-$, then $R_{23}$ or $R_{24}$ is different from a hydrogen atom;

if K denotes —$NR_{22}(X^-)_r$, then M=P=—CH, —CR;

if M denotes —$NR_{22}(X^-)_r$, then K=P=—CH, —CR;

if P denotes —$NR_{22}(X^-)_r$, then K=M and denote —CH or —CR;

if Z denotes a sulphur atom with $R_{21}$ denoting $C_1$–$C_4$ alkyl, then $R_{20}$ is different from a hydrogen atom;

if Z denotes —$NR_{22}$ with $R_{19}$ denoting $C_2$–$C_4$ alkyl, then at least one of the $R_{18}$, $R_{20}$ or $R_{21}$ radicals of the group having the structure $G_2$ is different from a $C_1$–$C_4$ alkyl radical;

the symbol J represents:

(a) a group having the following structure $J_1$:

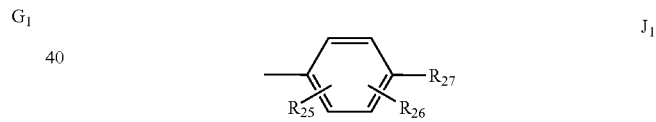
$J_1$ in which structure $J_1$, $R_{25}$ represents a hydrogen atom, a halogen atom chosen from chlorine, bromine, iodine and fluorine, a $C_1$–$C_4$ alkyl radical, a $C_1$–$C_4$ alkoxy radical, a radical —OH, —$NO_2$, —$NHR_{28}$, —$NR_{29}R_{30}$, —NHCO($C_1$–$C_4$alkyl), or forms with $R_{26}$ a 5- or 6-membered ring containing or otherwise one or more heteroatoms chosen from nitrogen, oxygen or sulphur;

$R_{26}$ represents a hydrogen atom, a halogen atom chosen from chlorine, bromine, iodine and fluorine, a $C_1$–$C_4$ alkyl or $C_1$–$C_4$ alkoxy radical, or forms with $R_{27}$ or $R_{28}$ a 5- or 6-membered ring containing or otherwise one or more heteroatoms chosen from nitrogen, oxygen or sulphur;

$R_{27}$ represents a hydrogen atom, an —OH radical, an —$NHR_{28}$ radical, an —$NR_{29}R_{30}$ radical;

$R_{28}$ represents a hydrogen atom, a $C_1$–$C_4$ alkyl radical, a $C_1$–$C_4$ monohydroxyalkyl radical, a $C_2$–$C_4$ polyhydroxyalkyl radical, a phenyl radical;

$R_{29}$ and $R_{30}$, which are identical or different, represent a $C_1$–$C_4$ alkyl radical, a $C_1$–$C_4$ monohydroxyalkyl radical, a $C_2$–$C_4$ polyhydroxyalkyl radical;

(b) a 5- or 6-membered nitrogen-containing heterocycle group which is capable of containing other heteroatoms and/or carbonyl-containing groups and which may be substituted with one or more $C_1$–$C_4$ alkyl, amino or phenyl radicals, and in particular a group having the following structure $J_2$:

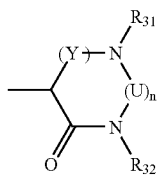

in which structure $J_2$, $R_{31}$ and $R_{32}$, which are identical or different, represent a hydrogen atom, a $C_1$–$C_4$ alkyl radical, a phenyl radical;

Y denotes the —CO— radical or the radical

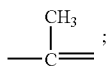

n=0 or 1, with, when n denotes 1, U denotes the —CO— radical.

In the structures (I) to (IV) defined above, the $C_1$–$C_4$ alkyl or alkoxy group preferably denotes methyl, ethyl, butyl, methoxy or ethoxy.

The cationic direct dyes of formulae (I), (II), (III) and (III') which can be used in the dyeing compositions in accordance with the invention are known compounds which are described, for example, in patent applications WO 95/01772, WO 95/15144 and EP-A-O 714 954. Those of formula (IV) that are useable in the dye compositions of the invention are identified compounds described in, for example, the patent applications FR-2189006, FR-2285851, and FR-2140205 and their certificates of addition.

Among the direct cationic dyes of formula (I) that are useable in the dye compositions of the invention, the compounds based on the following structures (I1) to (I54) can be specifically noted.

(I1)
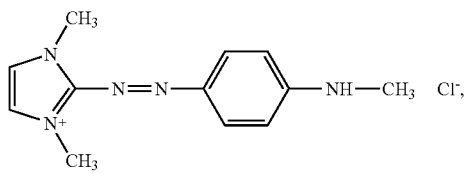

(I2)
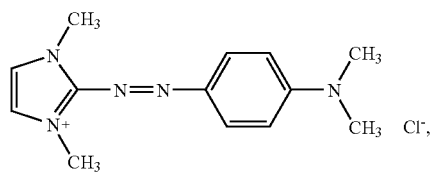

(I3)
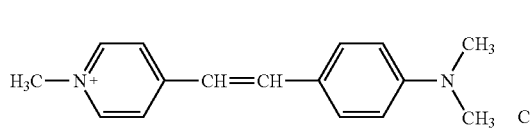

(I4)
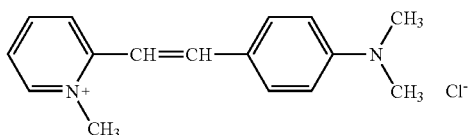

(I5)
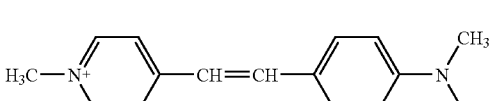

(I6)
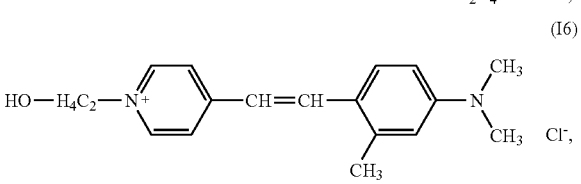

(I7)
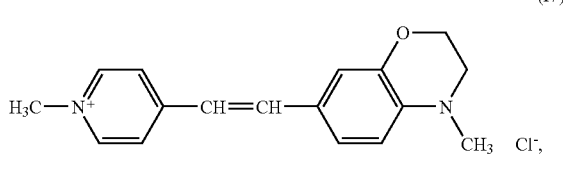

(I8)
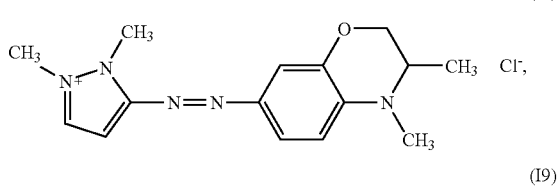

(I9)
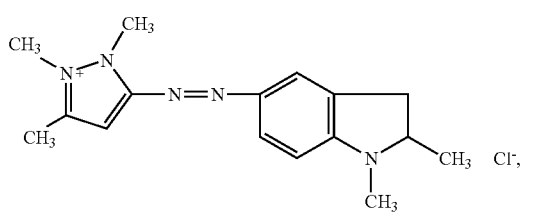

(I10)
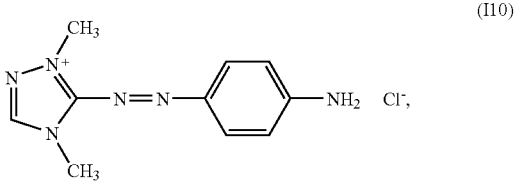

(I11)
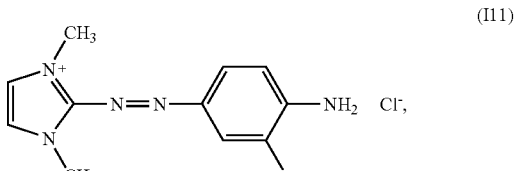

(I12)
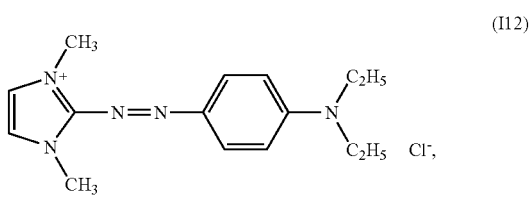

-continued
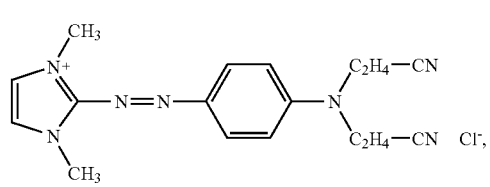
(I13)
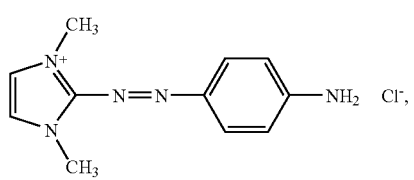
(I14)
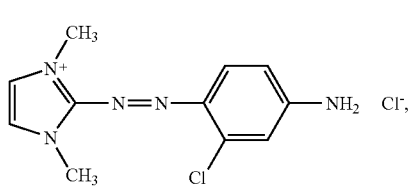
(I15)
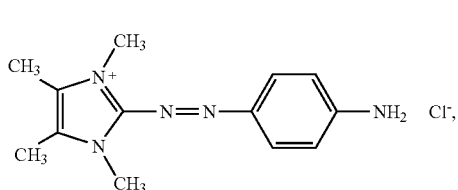
(I16)
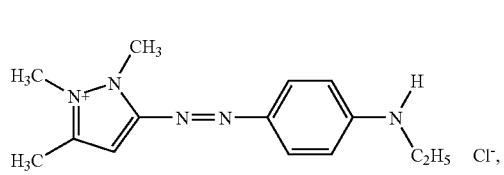
(I17)
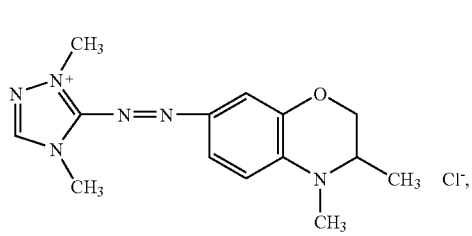
(I18)
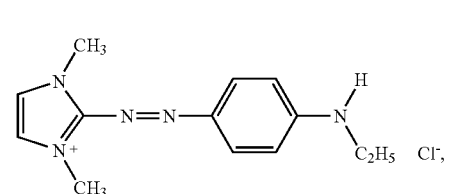
(I19)
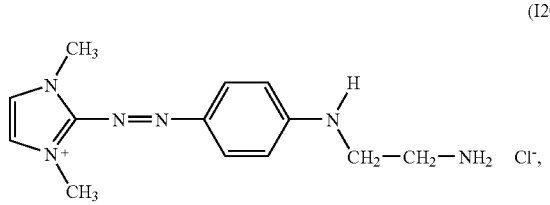
(I20)
-continued
(I21)
(I22)
(I23)
(I24)
(I25)
(I26)
(I27)
(I28)
(I29)

-continued

-continued (I48) [structure]

(I49) [structure]

(I50) [structure]

(I51) [structure]

(I52) [structure]

(I53) [structure]

(I54) [structure]

Among the compounds having the structures (I1) to (I54) which are described above, the compounds corresponding to the structures (I1), (I2), (I14) and (I31) are most particularly preferred.

Among the cationic direct dyes of formula (II) which can be used in the dyeing compositions in accordance with the invention, there may be mentioned more particularly the compounds corresponding to the following structures (II1) to (II9):

(II1) [structure]

(II2) [structure]

(II3) [structure]

(II4) [structure]

(II5) [structure]

(II6) [structure]

(II7) [structure]

(II8) [structure]

(II9) [structure]

Among the cationic direct dyes of formula (III) which can be used in the dyeing compositions in accordance with the invention, there may be mentioned more particularly the compounds corresponding to the following structures (III1) to (III18):

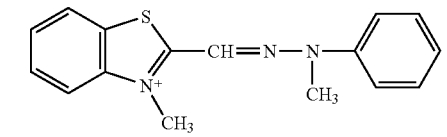 (III1)

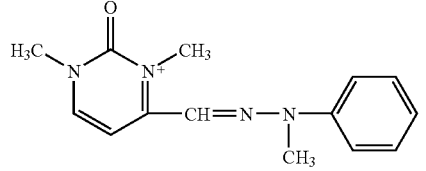 (III2)

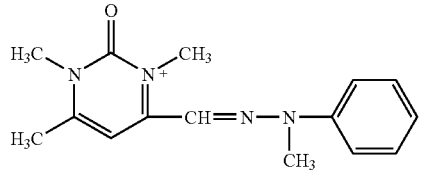 (III3)

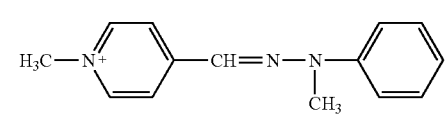 (III4)

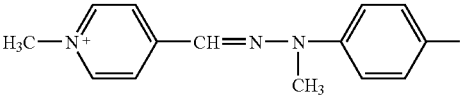 (III5)

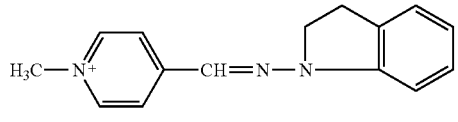 (III6)

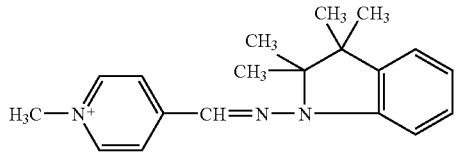 (III7)

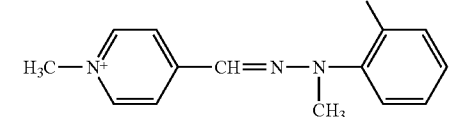 (III8)

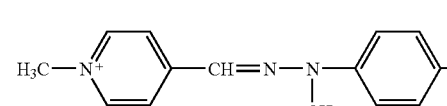 (III9)

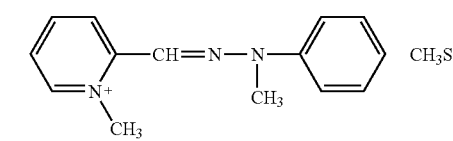 (III10)

-continued

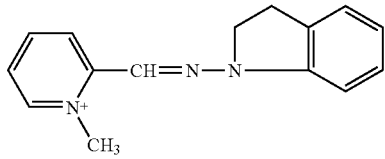 (III11)

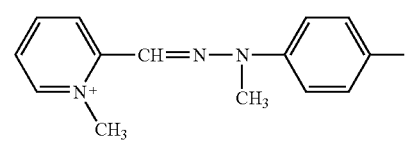 (III12)

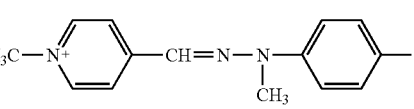 (III13)

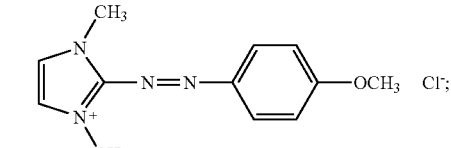 (III14)

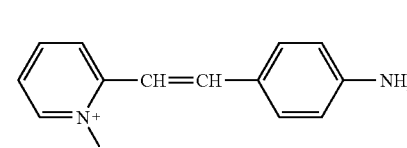 (III15)

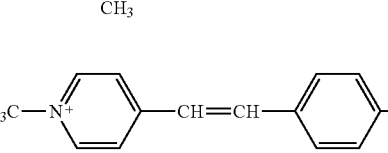 (III16)

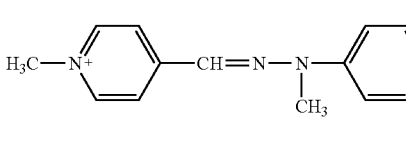 (III17)

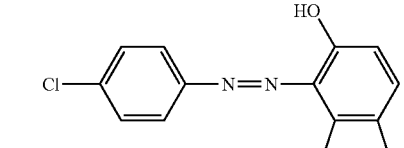 (III18)

Among the particular compounds having the structures (III1) to (III18) which are described above, the compounds corresponding to the structures (III4), (III5) and (III13) are most particularly preferred.

Among the cationic direct dyes of formula (III') which can be used in the dyeing compositions in accordance with the invention, there may be mentioned more particularly the compounds corresponding to the following structures (III'1) to (III'3)

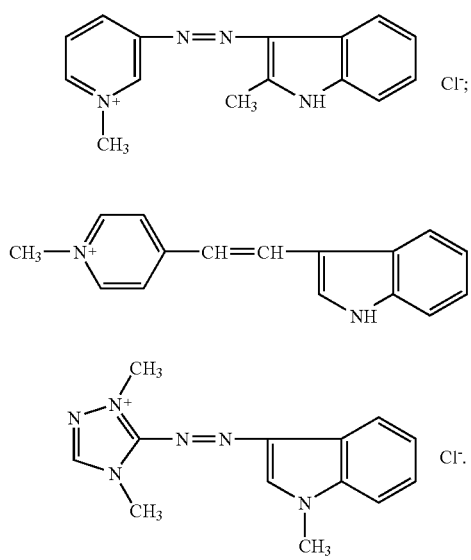
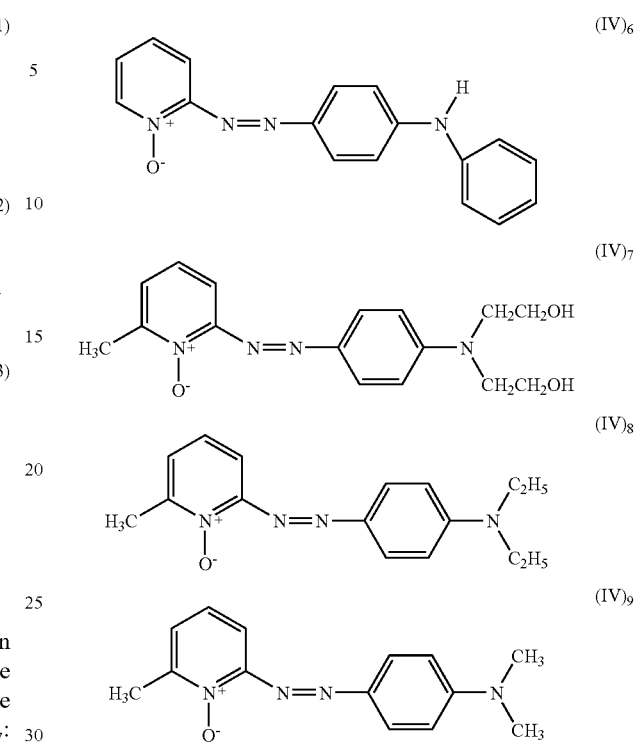
Among the cationic direct dyes of formula (IV) which can be used in the dyeing compositions in accordance with the invention, there may be mentioned more particularly the compounds having the following structures $(IV)_1$ to $(IV)_{77}$:
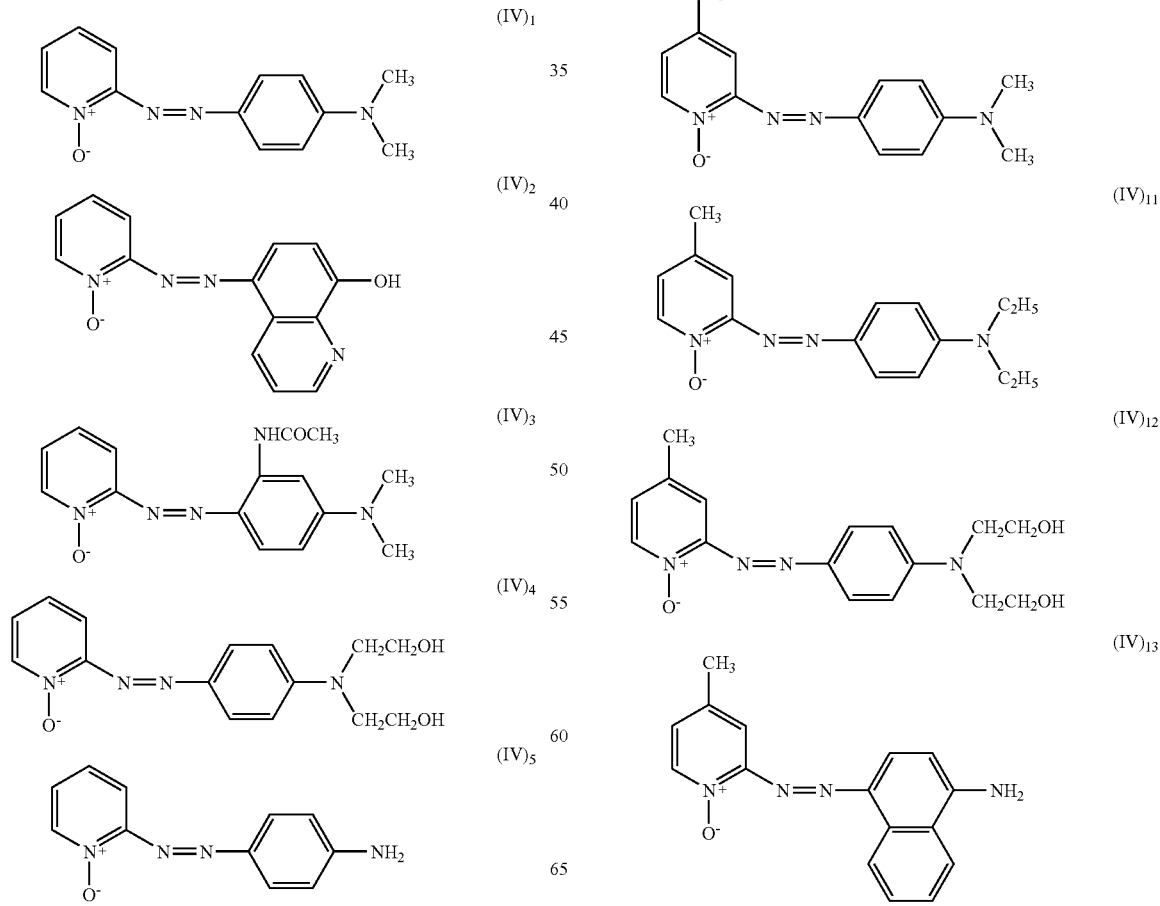

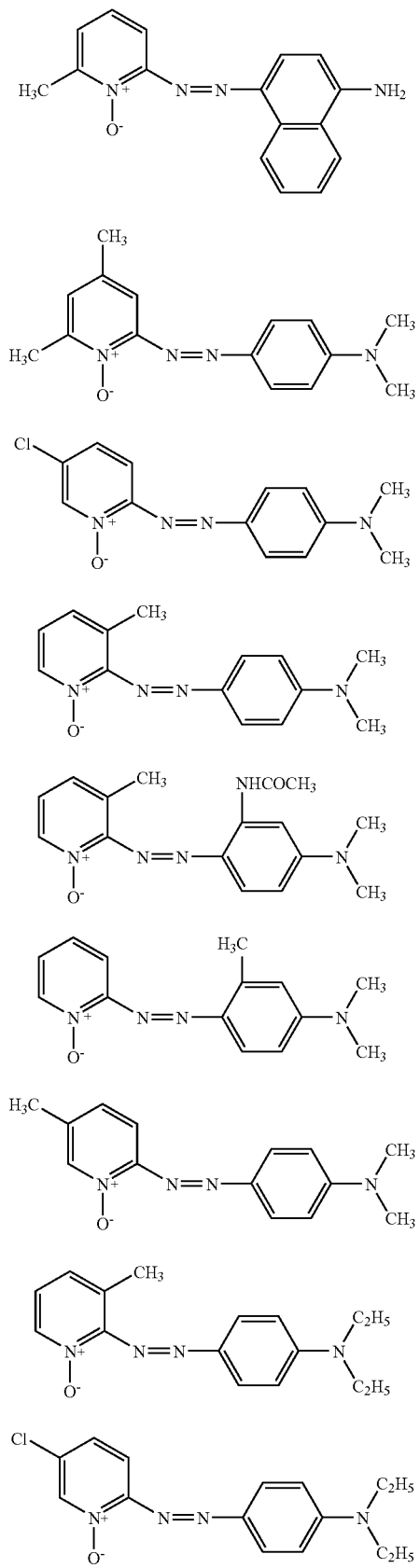
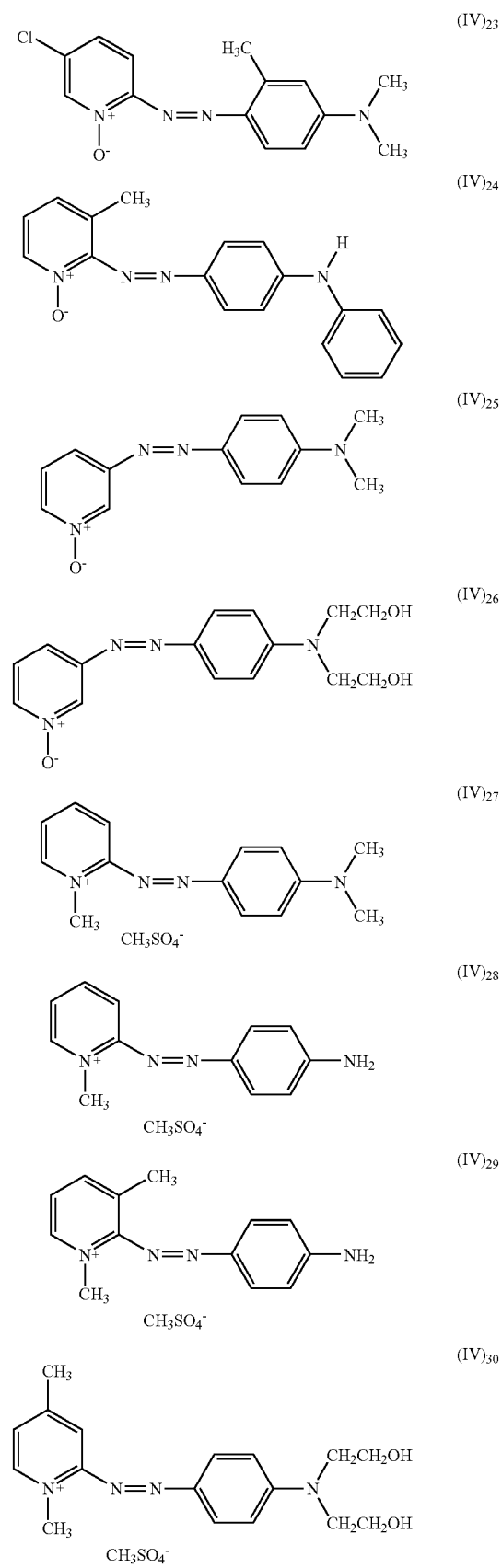

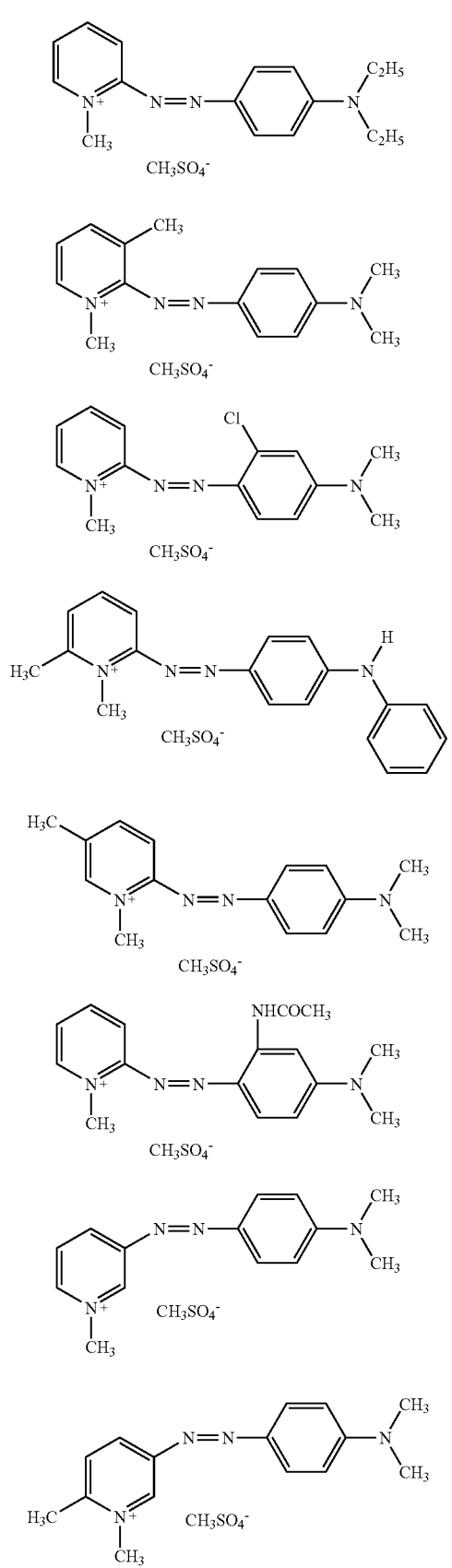

-continued
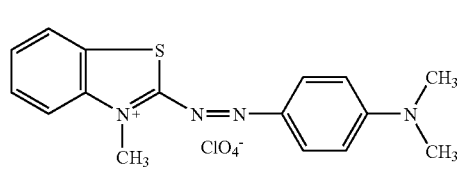 (IV)₄₆
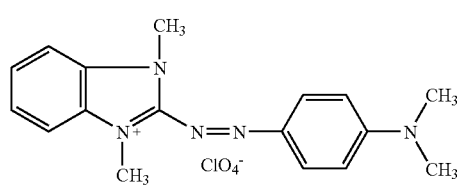 (IV)₄₇
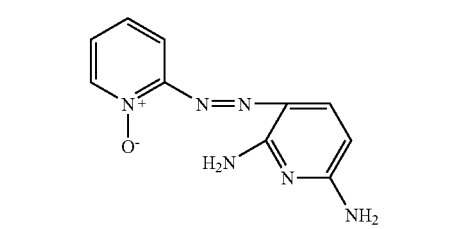 (IV)₄₈
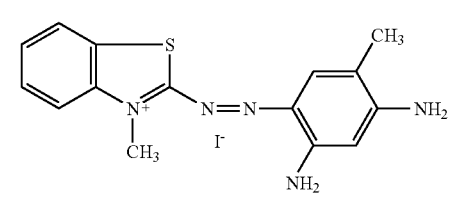 (IV)₄₉
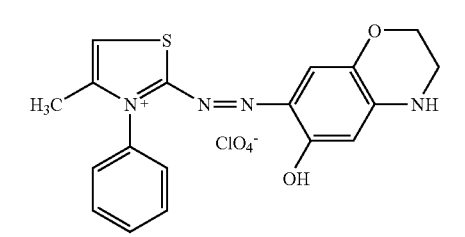 (IV)₅₀
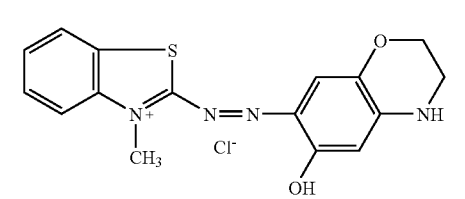 (IV)₅₁
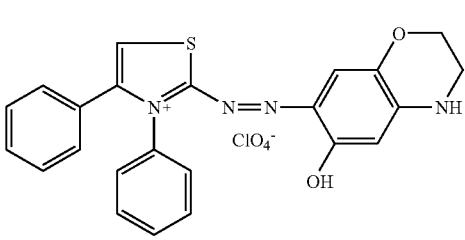 (IV)₅₂
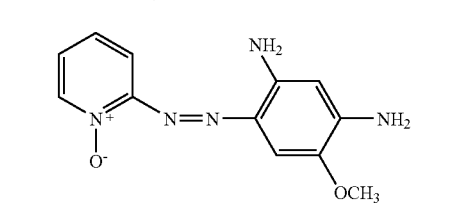 (IV)₅₃
-continued
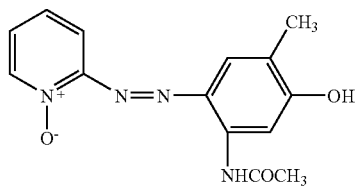 (IV)₅₄
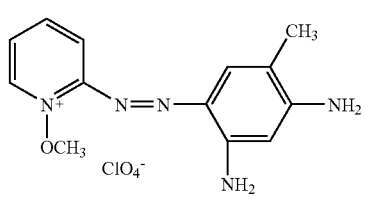 (IV)₅₅
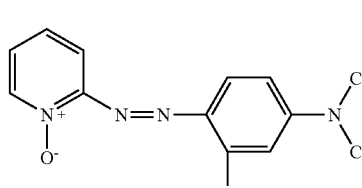 (IV)₅₆
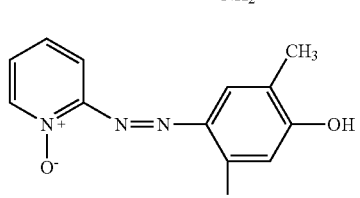 (IV)₅₇
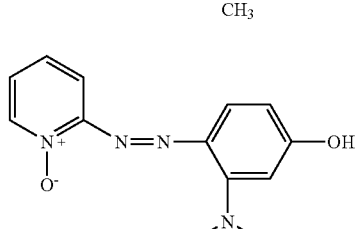 (IV)₅₈
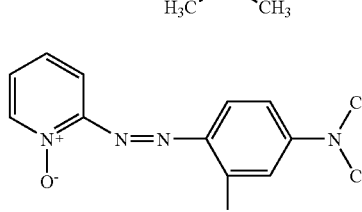 (IV)₅₉
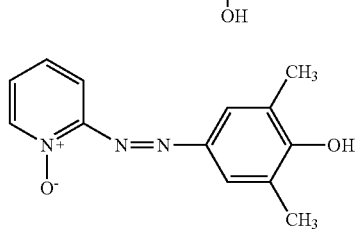 (IV)₆₀
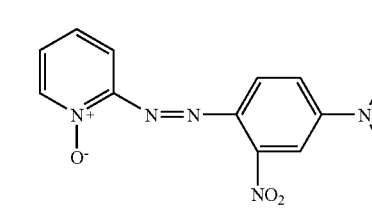 (IV)₆₁

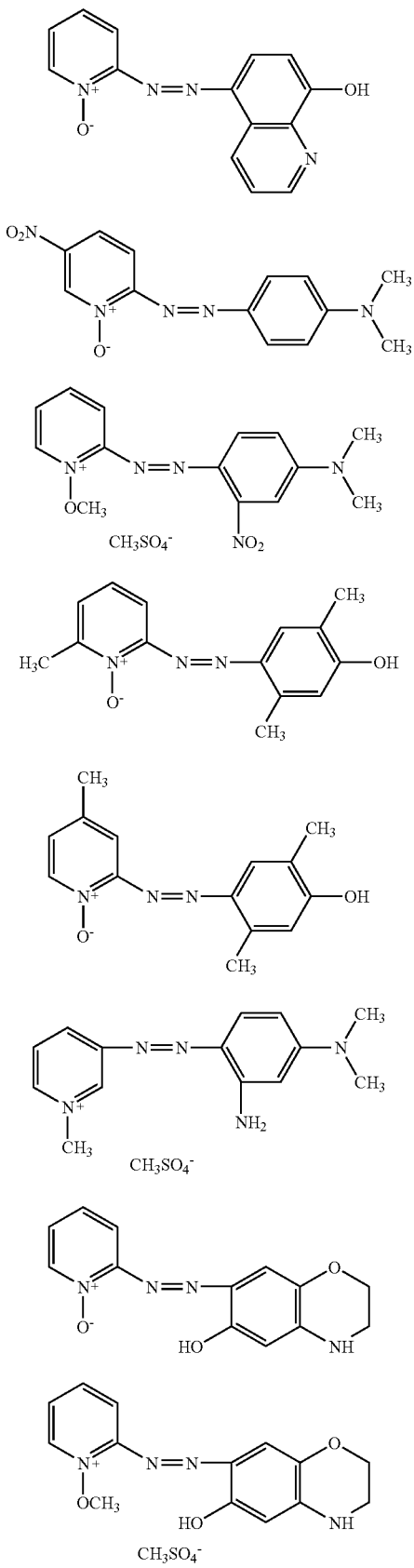
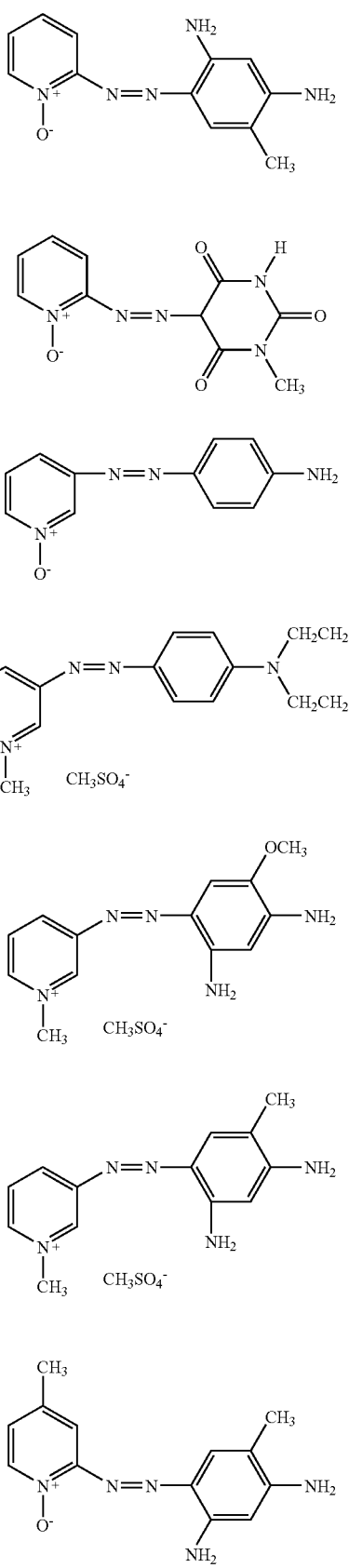

-continued

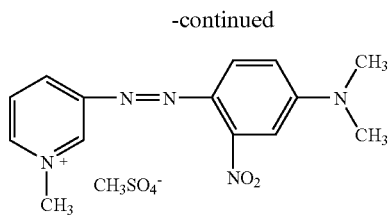
(IV)₇₇

The cationic direct dye(s) used according to the invention preferably represent from 0.001 to 10% by weight approximately of the total weight of the dyeing composition and still more preferably from 0.005 to 5% by weight approximately of this weight.

(ii) The quaternary ammonium salts which can be used according to the present invention are chosen from the group consisting of:

(ii)₁—those of the following formula (V):

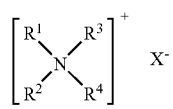
(V)

in which
the radicals $R^1$ and $R^4$, which are identical or different, denote a saturated or unsaturated, linear or branched, aliphatic hydrocarbon radical comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among $R^1$, $R^2$, $R^3$ and $R^4$ denoting a radical comprising from 8 to 30 carbon atoms;
$X^-$ is an anion chosen from the group comprising halides, phosphates, acetates, lactates and alkyl sulphates;
Among them, there may be mentioned, for example, (a) the dialkyldimethylammonium or alkyltrimethylammonium salts in which the alkyl radical comprises from about 12 to about 22 carbon atoms, such as the distearyldimethylammonium, cetyltrimethylammonium or behenyltrimethylammonium chlorides, (b) the di($C_1$–$C_2$ alkyl) ($C_{12}$–$C_{22}$ alkyl)hydroxy($C_1$–$C_2$ alkyl) ammonium salts such as oleocetylhydroxyethylammonium chloride, or alternatively (c) the stearamidopropyldimethyl (myristyl acetate) ammonium chloride of formula:

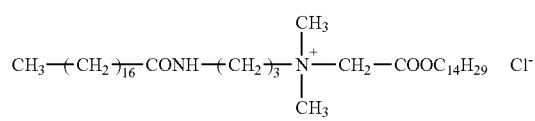

sold under the trademark CERAPHYL 70 by the company VAN DYK.

(ii)₂—the imidazolium salts of the following formula (VI):

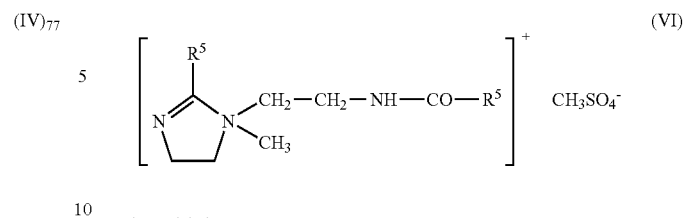
(VI)

in which,
$R^5$ is chosen from the alkenyl and/or alkyl radicals comprising from 13 to 31 carbon atoms and derived from tallow fatty acids, such as the product sold under the trademark "REWOQUAT W 75000 " by the company REWO;

(ii)₃—the quaternary diammonium salts of the following formula (VII):

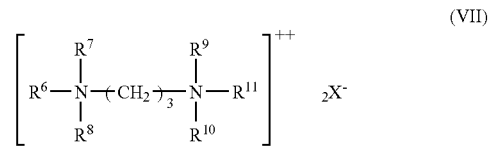
(VII)

in which,
$R^6$ denotes an aliphatic radical comprising from about 16 to 30 carbon atoms, $R^7$, $R^8$, $R^9$, $R^{10}$ and $R^{11}$ are chosen from hydrogen or an alkyl radical comprising from 1 to 4 carbon atoms, and $X^-$ is an anion chosen from the group comprising halides, acetates, phosphates and sulphates. Such quaternary diammonium salts comprise in particular propanetallowdiammonium dichloride.

According to the present invention, the quaternary ammonium salts of formula (V) are preferred in which $R^1$ to $R^4$, which are identical or different, denote alkyl or hydroxyalkyl radicals comprising from about 12 to about 22 carbon atoms, and in particular behenyltrimethylammonium chloride, cetyltrimethylammonium chloride and oleocetyldimethylhydroxyethylammonium chloride.

The quaternary ammonium salt(s) (ii) used according to the invention preferably represent from 0.01 to 10% by weight approximately of the total weight of the dyeing composition and still more preferably from 0.05 to 5% by weight approximately of this weight.

The appropriate dyeing medium (or carrier) generally consists of water or of a mixture of water and of at least one organic solvent for solubilizing the compounds which would not be sufficiently soluble in water. As organic solvent, there may be mentioned for example the $C_1$–$C_4$ lower alkanols such as ethanol and isopropanol, the aromatic alcohols such as benzyl alcohol as well as similar products and mixtures thereof.

The solvents may be present in proportions preferably of between 1 and 40% by weight approximately relative to the total weight of the dyeing composition, and still more preferably between 5 and 30% by weight approximately.

The pH of the dyeing composition in accordance with the invention is generally between 2 and 11 approximately, and preferably between 5 and 10 approximately. It may be adjusted to the desired value by means of acidifying or alkalinizing agents normally used in dyeing keratinous fibres.

Among the acidifying agents, there may be mentioned, by way of example, the inorganic or organic acids such as hydrochloric acid, orthophosphoric acid, sulphuric acid, carboxylic acids such as acetic acid, tartaric acid, citric acid, lactic acid, sulphonic acids.

Among the alkalinizing agents, there may be mentioned, by way of example, aqueous ammonia, alkali metal carbonates, alkanolamines such as mono-, di- and triethanolamines as well as derivatives thereof, sodium or potassium hydroxides and the compounds having the following formula (VIII):

in which W is a propylene residue which is optionally substituted with a hydroxyl group or a $C_1$–$C_6$ alkyl radical; $R^{12}$, $R^{13}$, $R^{14}$ and $R^{15}$, which are identical or different, represent a hydrogen atom, a $C_1$–$C_6$ alkyl radical or a $C_1$–$C_6$ hydroxyalkyl radical.

The dyeing composition in accordance with the invention may, in addition to the cationic direct dye(s) (i) defined above, contain one or more additional direct dyes which may for example be chosen from the nitrobenzene dyes, the anthraquinone dyes, the naphthoquinone dyes, the triarylmethane dyes, the xanthene dyes, the noncationic azo dyes.

When it is intended for oxidation dyeing, the dyeing composition in accordance with the invention contains, in addition to the cationic direct dye(s) (i), one or more oxidation bases chosen from the oxidation bases conventionally used for oxidation dyeing and among which there may be mentioned in particular the para-phenylenediamines, the bis-phenylalkylenediamines, the para-aminophenols, the ortho-aminophenols and the heterocyclic bases. When they are used, the oxidation base(s) preferably represent from 0.0005 to 12% by weight approximately of the total weight of the dyeing composition, and still more preferably from 0.005 to 6% by weight approximately of this weight.

When it is intended for oxidation dyeing, the dyeing composition in accordance with the invention may also contain, in addition to the cationic direct dye (i) and the quaternary ammonium salt (ii) as well as oxidation bases, one or more couplers so as to modify or increase the shimmer of the shades obtained using the cationic direct dye(s) (i) and the oxidation base(s).

The couplers which can be used in the dyeing composition in accordance with the invention may be chosen from the couplers conventionally used in oxidation dyeing and among which there may be mentioned in particular the meta-phenylenediamines, the meta-aminophenols, the meta-diphenols and the heterocyclic couplers.

When they are present, the coupler(s) preferably represent from 0.0001 to 10% by weight approximately of the total weight of the dyeing composition and still more preferably from 0.005 to 5% by weight approximately of this weight.

The dyeing composition in accordance with the invention may also contain various adjuvants which are conventionally used in hair-dyeing compositions, such as antioxidants, penetrating agents, sequestrants, perfumes, buffers, dispersing agents, film-forming agents, ceramides, preservatives, screening agents and opacifying agents.

Of course, persons skilled in the art will be careful to choose this or these optional additional compounds such that the advantageous properties intrinsically attached to the dyeing composition in accordance with the invention are not, or not substantially, altered by the addition(s) envisaged.

The dyeing composition according to the invention may be provided in various forms, such as in the form of liquids, shampoos, creams, gels, or in any other form appropriate for dyeing keratinous fibres, and in particular human hair. It may be obtained by freshly mixing a composition, which is optionally pulverulent, containing the cationic direct dye(s) with a composition containing the quaternary ammonium salt.

When the combination of the cationic direct dye (i) and of the quaternary ammonium salt (ii) according to the invention is used in a composition intended for oxidation dyeing (one or more oxidation bases are then used, optionally in the presence of one or more couplers) or when it is used in a composition intended for direct lightening dyeing, then the dyeing composition in accordance with the invention contains, in addition, at least one oxidizing agent chosen for example from hydrogen peroxide, urea peroxide, alkali metal bromates, persalts such the perborates and persulphates, and enzymes such as peroxidases, laccases and oxidoreductases containing two electrons. The use of hydrogen peroxide or of enzymes is particularly preferred.

Another subject of the invention is a method of dyeing keratinous fibres and in particular human keratinous fibres such as hair using the dyeing composition as defined above.

According to a first variant of this dyeing method in accordance with the invention, at least one dyeing composition as defined above is applied to the fibres for a sufficient time to develop the desired colour, after which they are rinsed, optionally washed with shampoo, rinsed again and dried.

The time necessary for the development of the colour on the keratinous fibres is generally between 3 and 60 minutes and still more preferably 5 and 40 minutes.

According to a second variant of this dyeing method in accordance with the invention, at least one dyeing composition as defined above is applied to the fibres for a sufficient time to develop the desired colour, with no final rinsing.

According to a particular embodiment of this dyeing method, and when the dyeing composition in accordance with the invention contains at least one oxidation base and at least one oxidizing agent, the dyeing method comprises a preliminary stage consisting of storing in a separate form, on the one hand, a composition (A1) comprising, in an appropriate dyeing medium, at least one cationic direct dye (i) as defined above and at least one oxidation base and, on the other hand, a composition (B1) containing, in an appropriate dyeing medium, at least one oxidizing agent, and then mixing them at the time of use before applying this mixture to the keratinous fibres, the composition (A1) or the composition (B1) containing the quaternary ammonium salt (ii) as defined above.

According to another particular embodiment of this dyeing method, and when the dyeing composition in accordance with the invention contains at least one oxidizing agent, the dyeing method comprises a preliminary stage consisting of storing in a separate form, on the one hand, a composition (A2) comprising, in an appropriate dyeing medium, at least one cationic direct dye (i) as defined above and, on the other hand, a composition (B2) containing, in an appropriate dyeing medium, at least one oxidizing agent, and then mixing them at the time of use before applying this mixture to the keratinous fibres, the composition (A2) or the composition (B2) containing the quaternary ammonium salt as defined above.

Another subject of the invention is a multicompartment device or dyeing "kit" or any other multicompartment packaging system in which a first compartment contains composition (A1) or (A2) as defined above and a second compartment contains composition (B1) or (B2) as defined above. These devices may be equipped with a means allowing the desired mixture to be delivered to the hair, such as the devices described in patent FR-2,586,913 in the applicant's name.

The following examples are intended to illustrate the invention without, however, limiting the scope thereof.

EXAMPLES

Examples 1 to 3

The three direct dyeing compositions which are assembled in the following table were prepared:

(All Contents Expressed in Grams)

|  | EXAMPLES NO. | | |
| --- | --- | --- | --- |
|  | 1 | 2 | 3 |
| Cationic direct dye of formula (I1) . . . | 0.20 | | |
| Cationic direct dye of formula (I14) . . . | | 0.20 | |
| Cationic direct dye of formula (IV)$_{27}$ . . . | | | 0.10 |
| Oleocetyldimethylhydroxyethyl)-ammonium chloride . . . | 2.0 AS* | | |
| Behenyltrimethylammonium chloride . . . | | 2.0 AS* | |
| Cetyltrimethylammonium chloride . . . | | | 2.0 AS* |
| Ethanol . . . | 10 | 10 | 10 |
| 2-amino-2-methyl-1-propanol qs . . . | pH 9 | pH 9 | pH 9 |
| Demineralized water qs . . . | 100 | 100 | 100 |

AS* denotes Active Substance

The above compositions were each applied for 30 minutes to locks of natural grey hair which is 90% white. The hair locks were then rinsed, washed with a standard shampoo and then dried.

The locks were dyed in the following shades:

| Examples | Shades obtained |
| --- | --- |
| 1 | dark red |
| 2 | dark orange |
| 3 | dark purple |

The invention claimed is:

1. A composition for the oxidation dyeing of keratinous fibers comprising, in a medium suitable for dyeing,
   (i) at least one cationic direct dye chosen from:
   a) cationic direct dyes of formula (I):

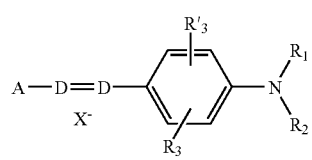
(I)

in which:

D is a nitrogen atom or a —CH group, $R_1$ and $R_2$, which are identical or different, are chosen from a hydrogen atom; a $C_1$–$C_4$ alkyl radical which is unsubstituted or substituted with a —CN, —OH or —NH$_2$ radical or form with each other or a carbon atom of the benzene ring a heterocycle optionally containing at least one of oxygen and nitrogen and which is unsubstituted or substituted with at least one $C_1$–$C_4$ alkyl radical; and a 4'-aminophenyl radical, $R_3$ and $R'_3$, which are identical or different, are chosen from a hydrogen atom; a halogen atom chosen from chlorine, bromine, iodine and fluorine; a cyano radical; a $C_1$–$C_4$ alkyl radical; a $C_1$–$C_4$ alkoxy radical; and an acetyloxy radical, $X^-$ is an anion, A is a group chosen from the following structures $A_1$ to $A_{19}$:

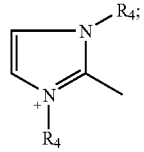
$A_1$

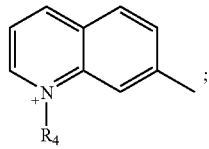
$A_2$

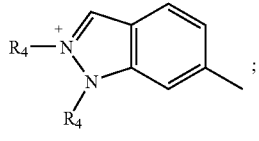
$A_3$

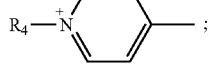
$A_4$

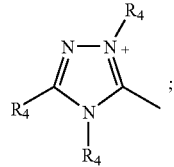
$A_5$

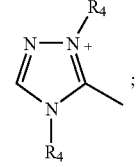
$A_6$

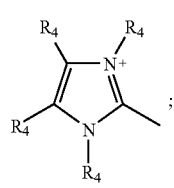
$A_7$

-continued

A8 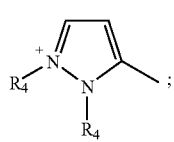

A9 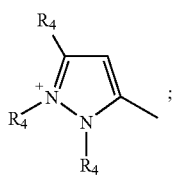

A10 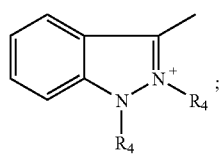

A11 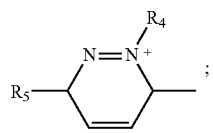

A12 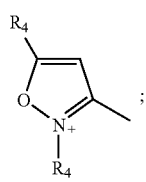

A13 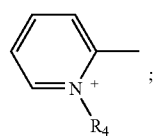

A14 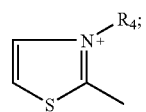

A15 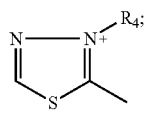

A16 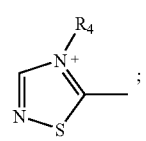

A17 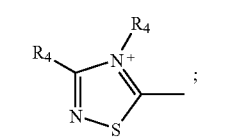

A18 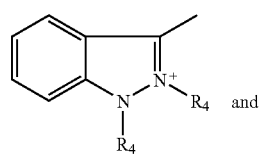 and

A19 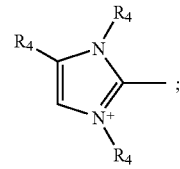

in which $R_4$ is a $C_1$–$C_4$ alkyl radical which is unsubstituted or substituted with a hydroxyl radical and $R_5$ is a $C_1$–$C_4$ alkoxy radical, with the proviso that when D represents —CH, A is $A_4$ or $A_{13}$ and $R_3$ is different from an alkoxy radical, then $R_1$ and $R_2$ are not simultaneously hydrogen atoms;

b) cationic direct dyes of formula (II):

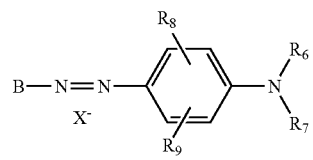

(II)

in which:

$R_6$ is a hydrogen atom or a $C_1$–$C_4$ alkyl radical, $R_7$ is chosen from a hydrogen atom; an alkyl radical which is unsubstituted or substituted with a —CN radical or with an amino group; and a 4'-aminophenyl radical, or forms with $R_6$ a heterocycle optionally containing at least one of oxygen and nitrogen and which is unsubstituted or substituted with a $C_1$–$C_4$ alkyl radical, $R_8$ and $R_9$, which are identical or different, are chosen from a hydrogen atom; a halogen atom chosen from bromine, chlorine, fluorine, and iodine; a $C_1$–$C_4$ alkyl radical; a $C_1$–$C_4$ alkoxy radical; and a —CN radical, X– is an anion, B represents a group chosen from the following structures B1 to B6:

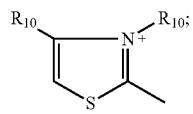 B1

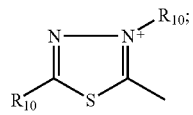 B2

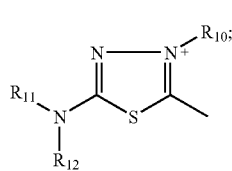 B3

-continued

B4

[structure: 2-methylquinolinium with N-R₁₀]

B5

[structure: R₁₀—N⁺ quinolinium, 4-methyl] and

B6

[structure: isothiazolium with R₁₀ substituents and methyl]

in which R₁₀ is a $C_1$–$C_4$ alkyl radical, $R_{11}$ and $R_{12}$, which are identical or different, are a hydrogen atom or a $C_1$–$C_4$ alkyl radical;

c) cationic direct dyes of the following formula (III) and formula (III'):

$$E-D_1=D_2-(N)_m-\text{[benzene with } R_{13}, R_{15}\text{]}$$
$$\text{with } R_{14} \text{ on N, } X^-$$
(III)

$$E-D_1=D_2-\text{[indene with } R_{16}, R_{17}\text{]}$$
$$X^-$$
(III')

in which:

$R_{13}$ is chosen from a hydrogen atom, a $C_1$–$C_4$ alkoxy radical, a halogen atom chosen from bromine, chlorine, fluorine, and iodine; and an amino radical, $R_{14}$ is a hydrogen atom, a $C_1$–$C_4$ alkyl radical or forms with a carbon atom of the benzene ring a heterocycle which is optionally oxygen-containing and is unsubstituted or substituted with at least one $C_1$–$C_4$ alkyl group, $R_{15}$ is a hydrogen or halogen atom chosen from bromine, chlorine, fluorine, and iodine, $R_{16}$ and $R_{17}$, which are identical or different, are a hydrogen atom or a $C_1$–$C_4$ alkyl radical, $D_1$ and $D_2$, which are identical or different, are a nitrogen atom or a —CH group, m=0 or 1, with the proviso that when $R_{13}$ is an unsubstituted amino group, then $D_1$ and $D_2$ simultaneously are —CH groups and m=0, $X^-$ is an anion, E is a group chosen from the following structures E1 to E8:

E1

[structure: R'—N⁺ pyridinium, 4-methyl]

E2

[structure: pyridinium with R', 2-methyl]

E3

[structure: pyrimidinone with R', R', methyl]

E4

[structure: pyrimidinone with R', R', R', methyl]

E5

[structure: hydroxy methyl indazolium with R', R']

E6

[structure: benzothiazolium with R', methyl]

E7

[structure: pyridinium with R', 3-methyl] and

E8

[structure: triazolium with R', R', methyl]

in which R' is a $C_1$–$C_4$ alkyl radical;

when m=0 and $D_1$ is a nitrogen atom, then E may also be a group having the following structure E9:

E9

[structure: imidazolium with R', R']

in which R' is a $C_1$–$C_4$ alkyl radical, and d) cationic direct dyes of formula (IV):

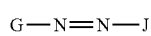  (IV)

in which:
the symbol G is a group chosen from the following structures $G_1$ to $G_3$:

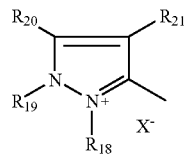 $G_1$

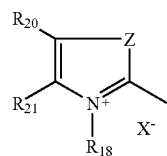 $G_2$

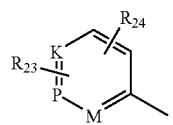 $G_3$ in which structures $G_1$ to $G_3$,
- $R_{18}$ is chosen from a $C_1$–$C_4$ alkyl radical; a phenyl radical which is unsubstituted or substituted with a $C_1$–$C_4$ alkyl radical or with a halogen atom chosen from chlorine, bromine, iodine and fluorine;
- $R_{19}$ is a $C_1$–$C_4$ alkyl radical or a phenyl radical;
- $R_{20}$ and $R_{21}$, which are identical or different, are chosen from a $C_1$–$C_4$ alkyl radical and a phenyl radical, or form together in $G_1$ a benzene ring which is substituted with at least one radical chosen from $C_1$–$C_4$ alkyl, $C_1$–$C_4$ alkoxy and $NO_2$ radicals, or form together in $G_2$ a benzene ring which is optionally substituted with at least one radical chosen from $C_1$–$C_4$ alkyl, $C_1$–$C_4$ alkoxy and $NO_2$ radicals;
- $R_{20}$ may also be a hydrogen atom;
- Z is an oxygen or sulphur atom or an —$NR_{19}$ group;
- M is a group chosen from —CH; —CR wherein R is $C_1$–$C_4$ alkyl; and —$NR_{22}(X^-)_r$;
- K is a group chosen from —CH; —CR wherein R is $C_1$–$C_4$ alkyl; and —$NR_{22}(X^-)_r$;
- P is a group chosen from —CH; —CR wherein R denotes $C_1$–$C_4$ alkyl; and —$NR_{22}(X^-)_r$ where r is zero or 1;
- $R_{22}$ is chosen from an $O^-$ atom, a $C_1$–$C_4$ alkoxy radical and a $C_1$–$C_4$ alkyl radical;
- $R_{23}$ and $R_{24}$, which are identical or different, are chosen from a hydrogen atom; a halogen atom chosen from chlorine, bromine, iodine and fluorine; a $C_1$–$C_4$ alkyl radical; a $C_1$–$C_4$ alkoxy radical; and an —$NO_2$ radical;
- $X^-$ is an anion;
wherein J is chosen from:
(a) a group having the following structure $J_1$:

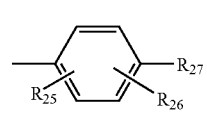 $J_1$ in which structure $J_1$,
- $R_{25}$ is chosen from a hydrogen atom; a halogen atom chosen from chlorine, bromine, iodine and fluorine; a $C_1$–$C_4$ alkyl radical; a $C_1$–$C_4$ alkoxy radical; and a radical chosen from —OH, —$NO_2$, —$NHR_{28}$, —$NR_{29}R_{30}$, and —NHCO($C_1$–$C_4$alkyl), or forms with $R_{26}$ a 5- or 6-membered ring optionally containing at least one heteroatom chosen from nitrogen, oxygen and sulphur;
- $R_{26}$ is chosen from a hydrogen atom; a halogen atom chosen from chlorine, bromine, iodine and fluorine; a $C_1$–$C_4$ alkyl radical; and a $C_1$–$C_4$ alkoxy radical, or forms with $R_{27}$ or $R_{28}$ a 5- or 6-membered ring optionally containing at least one heteroatom chosen from nitrogen, oxygen or sulphur;
- $R_{27}$ is chosen from a hydrogen atom, an —OH radical, an —$NHR_{28}$ radical, and an —$NR_{29}R_{30}$ radical;
- $R_{28}$ is chosen from a hydrogen atom, a $C_1$–$C_4$ alkyl radical, a $C_1$–$C_4$ monohydroxyalkyl radical, a $C_2$–$C_4$ polyhydroxyalkyl radical, and a phenyl radical;
- $R_{29}$ and $R_{30}$, which are identical or different, are chosen from a $C_1$–$C_4$ alkyl radical, a $C_1$–$C_4$ monohydroxyalkyl radical, and a $C_2$–$C_4$ polyhydroxyalkyl radical; and (b) a 5- or 6-membered nitrogen-containing heterocycle group which optionally contains additional heteroatoms, carbonyl-containing groups, or a mixture of additional heteroatoms and carbonyl-containing groups and which is unsubstituted or substituted with at least one radical chosen from $C_1$–$C_4$ alkyl, amino and phenyl radicals, (ii) at least one quaternary ammonium salt chosen from:

(ii)$_1$—quaternary ammonium salts of the following formula (V):

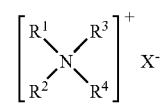 (V)

in which
the radicals $R^1$, $R^2$, $R^3$, and $R^4$, which are identical or different, are chosen from a saturated or unsaturated, linear or branched, aliphatic hydrocarbon radical comprising 1 to 30 carbon atoms; and a radical chosen from alkoxy, alkoxycarbonylalkyl, polyoxyalkylene, alkylamido, alkylamidoalkyl, hydroxyalkyl, aromatic, aryl and alkylaryl radicals comprising 12 to 30 carbon atoms, wherein at least one radical among $R^1$, $R^2$, $R^3$ and $R^4$ is a radical comprising 8 to 30 carbon atoms;
$X^-$ is an anion chosen from halides, phosphates, acetates, lactates and alkyl sulphates;

(ii)$_2$—imidazolium salts of the following formula (VI):

$$\left[ \begin{array}{c} R^5 \\ \diagup \\ N \\ \Vert \\ N \\ \diagdown \\ CH_3 \end{array} \diagdown CH_2-CH_2-NH-CO-R^5 \right]^+ \quad CH_3SO_4^- \quad (VI)$$

in which
R$^5$ is chosen from alkenyl radicals and alkyl radicals, said alkenyl radicals and alkyl radicals comprising 13 to 31 carbon atoms and being derived from tallow fatty acids;

(ii)$_3$—quaternary diammonium salts of the following formula (VII):

$$\left[ R^6 - \underset{R^8}{\overset{R^7}{\underset{|}{\overset{|}{N}}}} - (CH_2)_3 - \underset{R^{10}}{\overset{R^9}{\underset{|}{\overset{|}{N}}}} - R^{11} \right]^{++} \quad 2X^- \quad (VII)$$

in which
R$^6$ is a
n aliphatic radical comprising 16 to 30 carbon atoms,
R$^7$, R$^6$, R$^9$, R$^{10}$ and R$^{11}$ are chosen from hydrogen or an alkyl radical comprising 1 to 4 carbon atoms, and X$^-$ is an anion chosen from halides, acetates, phosphates and sulphates, and (iii) at least one oxidation base.

2. A composition according to claim 1, wherein in the definition of said at least one cationic direct dye of formulas (I), (II), (III), and (III'), X$^-$ is chosen from chloride, methylsulphate, and acetate.

3. A composition according to claim 1, wherein in the definition of said cationic direct dyes of formula (IV), in G$_1$ and G$_2$, X$^-$ is chosen from chloride, iodide, methylsulphate, ethylsulphate, acetate and perchlorate.

4. A composition according to claim 1, wherein in the definition of said cationic direct dyes of formula (IV), the 5- or 6-membered nitrogen containing heterocycle group of J is chosen from groups having the structure J$_2$ below:

$$\begin{array}{c} R_{31} \\ \diagup \\ (Y)-N \\ | \\ (U)_n \\ | \\ N \\ \diagdown \\ O \quad R_{32} \end{array} \quad J_2$$

in which structure J$_2$,
R$_{31}$ and R$_{32}$, which are identical or different, are chosen from a hydrogen atom; a C$_1$–C$_4$ alkyl radical, and a phenyl radical;

Y is a —CO— radical or the radical $$\begin{array}{c} CH_3 \\ | \\ -C= \end{array} \quad ;$$

and
n=0 or 1, wherein when n is 1, U is a —CO— radical.

5. A composition according to claim 1, wherein said at least one cationic direct dye is present in an amount ranging from 0.001 to 10% by weight of the total weight of the composition.

6. A composition according to claim 5, wherein said at least one cationic direct dye is present in an amount ranging from 0.005 to 5% by weight of the total weight of the composition.

7. A composition according to claim 1, wherein the quaternary ammonium salt of formula (V) is a dialkyldimethylammonium or alkyltrimethylammonium salt in which the alkyl radical comprises 12 to 22 carbon atoms.

8. A composition according to claim 7, wherein the quaternary ammonium salt of formula (V) is distearyldimethylammonium chloride, cetyltrimethylammonium chloride, or behenyltrimethylammonium chloride.

9. A composition according to claim 1, wherein the quaternary ammonium salt of formula (V) is a di(C$_1$–C$_2$ alkyl)(C$_{12}$–C$_{22}$alkyl)hydroxy(C$_1$–C$_2$alkyl)ammonium salt.

10. A composition according to claim 9, wherein the quaternary ammonium salt of formula (V) is oleocetyldimethylhydroxyethylammonium chloride.

11. A composition according to claim 1, wherein the quaternary ammonium salt of formula (V) is stearamidopropyldimethyl (myristyl acetate) ammonium chloride of formula:

$$CH_3-(CH_2)_{16}-CONH-(CH_2)_3-\underset{CH_3}{\overset{CH_3}{\underset{|}{\overset{|}{N^+}}}}-CH_2-COOC_{14}H_{29} \quad Cl^-.$$

12. A composition according to claim 1, wherein said at least one quaternary ammonium salt is present in an amount ranging from 0.01 to 10% by weight of the total weight of the composition.

13. A composition according to claim 12, wherein said at least one quaternary ammonium salt is present in an amount ranging from 0.05 to 5% by weight of the total weight of the composition.

14. A composition according to claim 1, wherein said medium suitable for dyeing comprises water or a mixture of water and at least one organic solvent.

15. A composition according to claim 1, wherein the composition has a pH ranging from 2 to 11.

16. A composition according to claim 15, wherein the pH ranges from 5 to 10.

17. A composition according to claim 1, wherein the composition further comprises at least one oxidizing agent.

18. A composition according to claim 17, wherein said at least one oxidizing agent is chosen from peroxides, alkali metal bromates, persalts, and enzymes.

19. A composition according to claim 18, wherein said peroxides are chosen from hydrogen peroxide and urea peroxide.

20. A composition according to claim 18, wherein said persalts are chosen from perborates and persulphates.

21. A composition according to claim 18, wherein said enzymes are chosen from peroxidases, laccases, and two-electron oxidoreductases.

22. A composition according to claim 1, wherein said keratinous fibers are human keratinous fibers.

23. A composition according to claim 22, wherein said human keratinous fibers are hair.

24. A composition according to claim 1, wherein the cationic direct dyes of formula (I) are chosen from the compounds corresponding to the following structures (I1) to (I54):

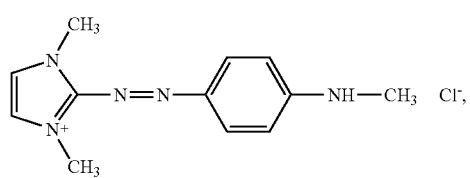
(I1)

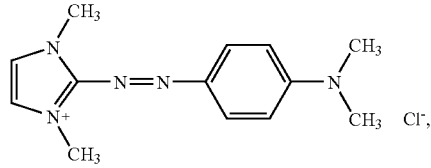
(I2)

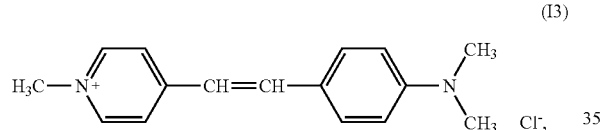
(I3)

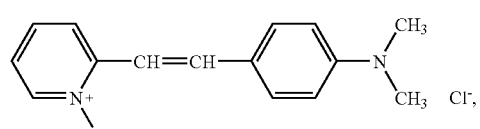
(I4)

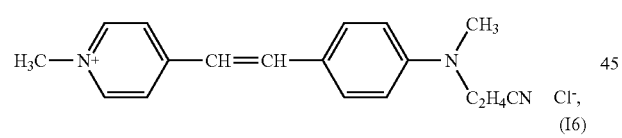
(I5)

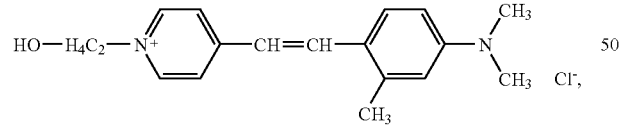
(I6)

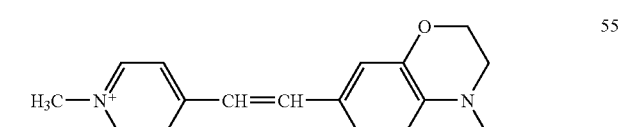
(I7)

(I8)

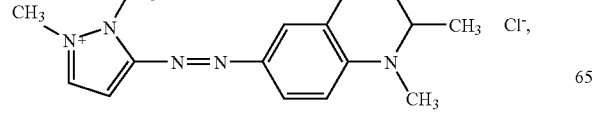

-continued

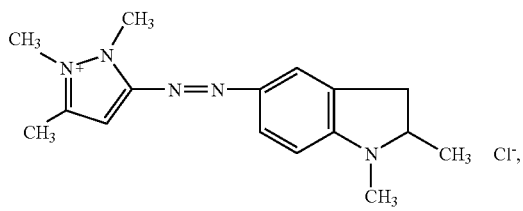
(I9)

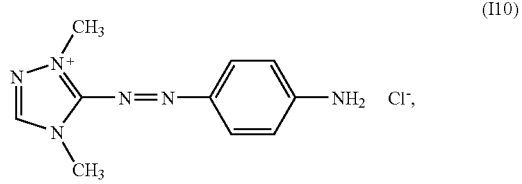
(I10)

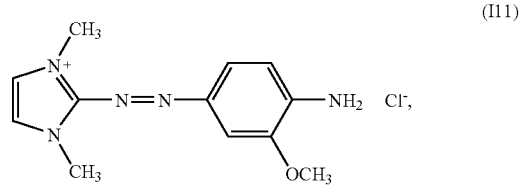
(I11)

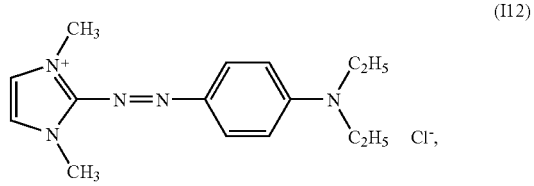
(I12)

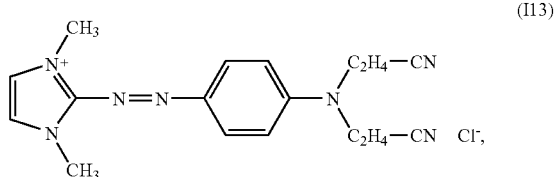
(I13)

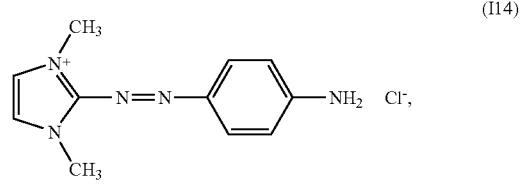
(I14)

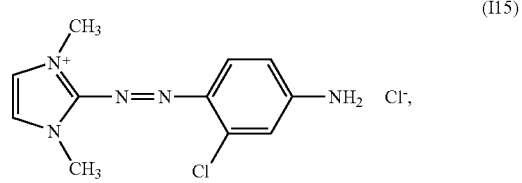
(I15)

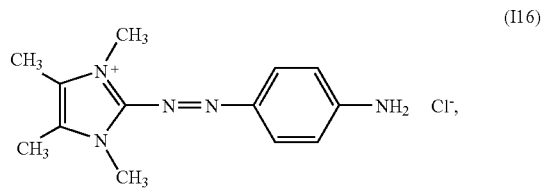
(I16)

-continued
(I17) 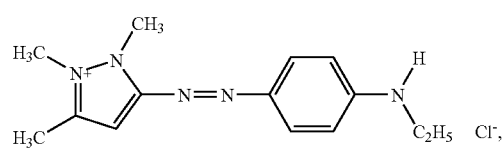
(I18) 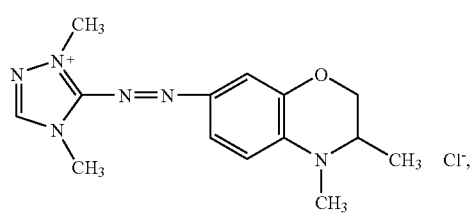
(I19) 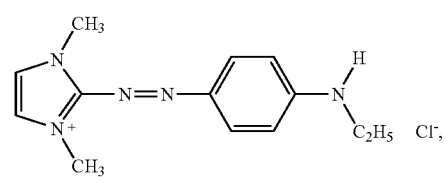
(I20) 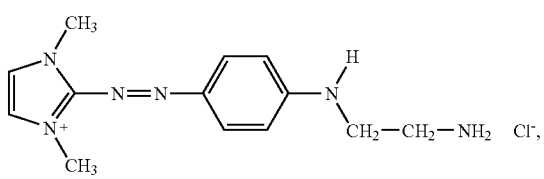
(I21) 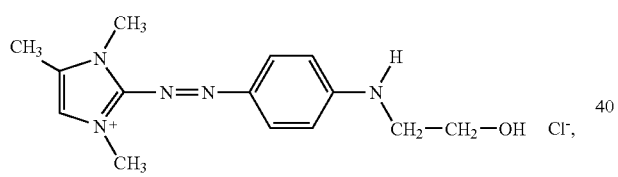
(I22) 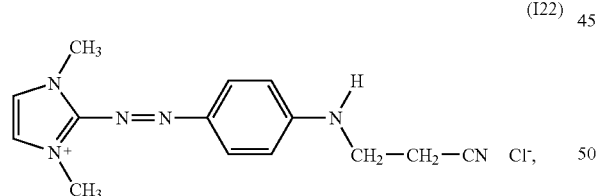
(I23) 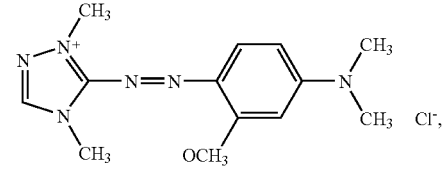
(I24) 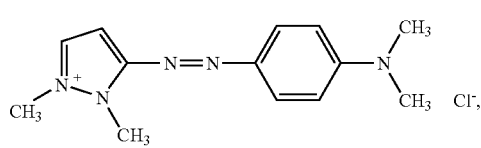
-continued
(I25) 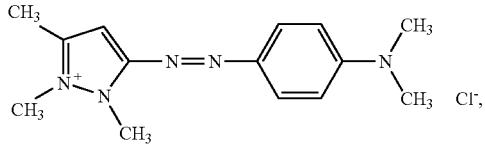
(I26) 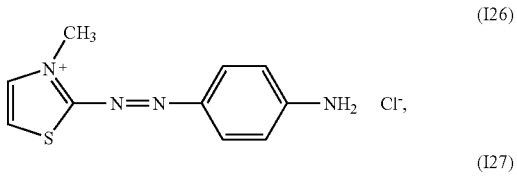
(I27)
(I28)
(I29)
(I30)
(I31)
(I32)
(I33) 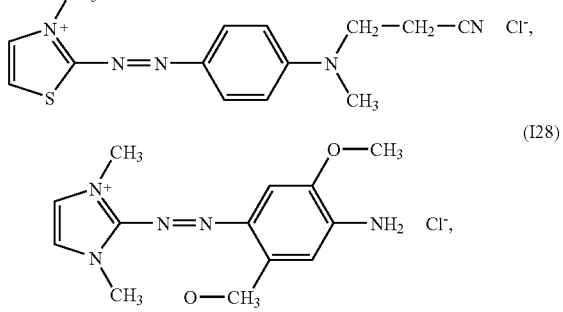

-continued
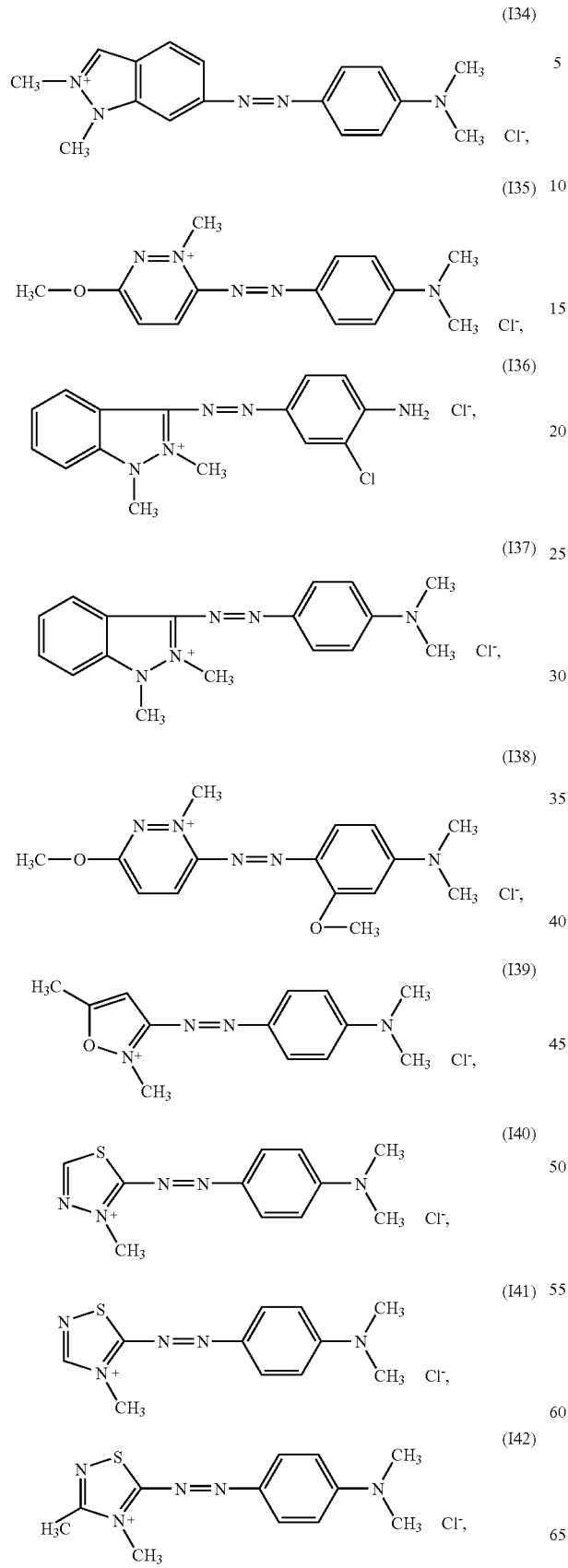
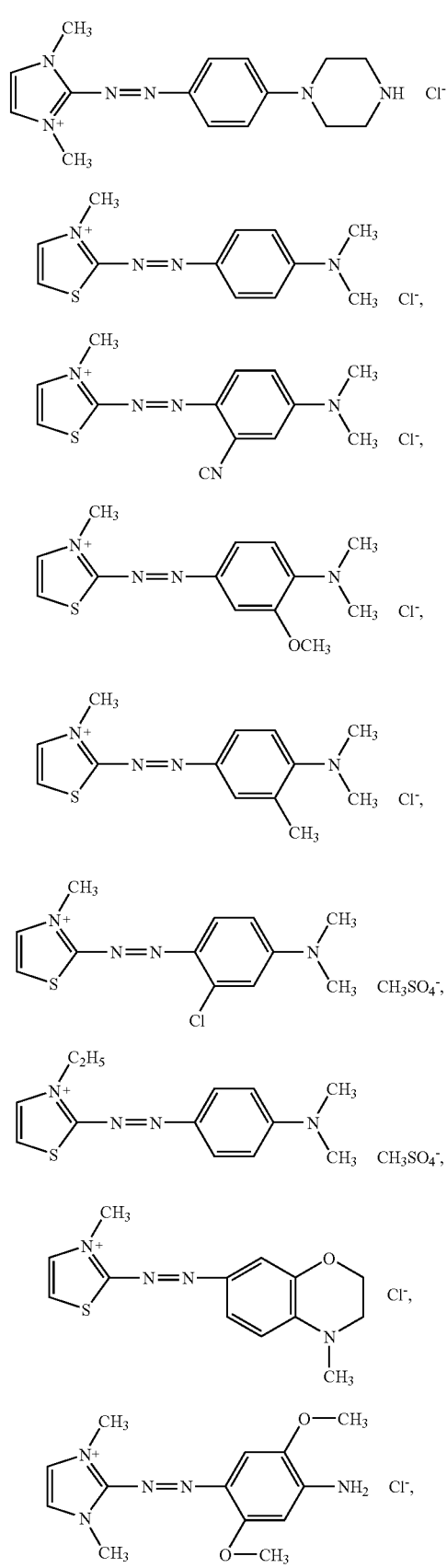

-continued

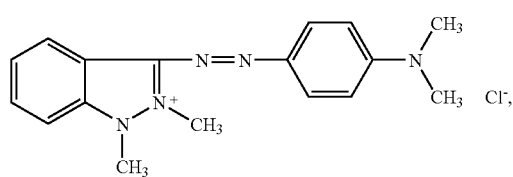 (I52)

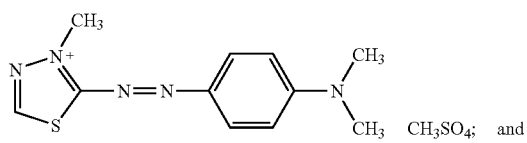 (I53)

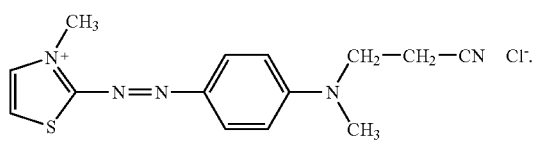 (I54)

25. A composition according to claim 24, wherein the cationic direct dyes are chosen from the compounds having structures (I1), (I2), (I14), and (I31).

26. A composition according to claim 1, wherein the cationic direct dyes of formula (II) are chosen from the compounds corresponding to the following structures (II1) to (II9)

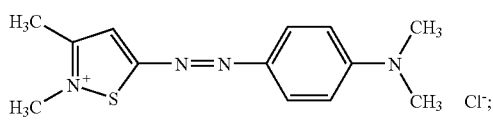 (II1)

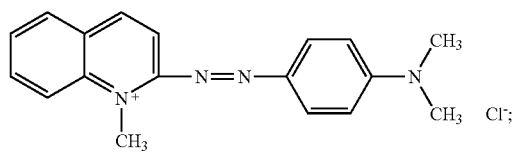 (II2)

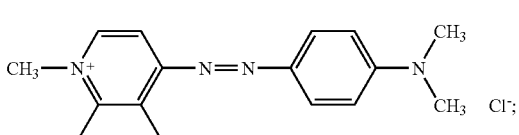 (II3)

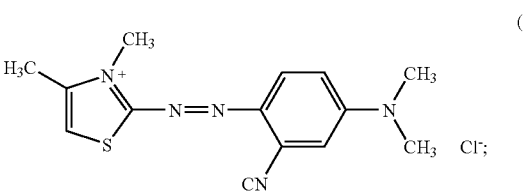 (II4)

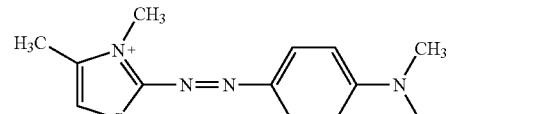 (II5)

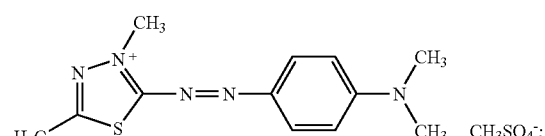 (II6)

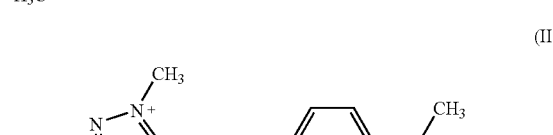 (II7)

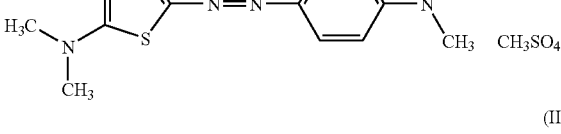 (II8)

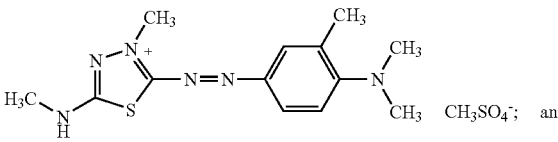 (II9)

27. A composition according to claim 1, wherein the cationic direct dyes of formula (III) are chosen from the compounds corresponding to the following structures (III1) to (III18):

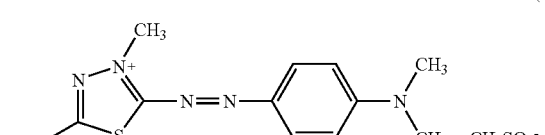 (III1)

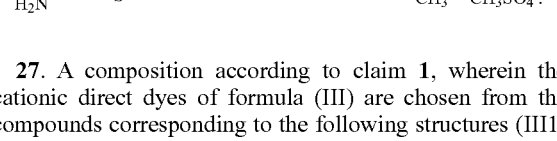 (III2)

 (III3)

-continued (III4) H₃C—N⁺(pyridine)—CH=N—N(CH₃)(phenyl)  CH₃SO₄⁻;

(III5) H₃C—N⁺(pyridine)—CH=N—N(CH₃)(C₆H₄—OCH₃)  Cl⁻;

(III6) H₃C—N⁺(pyridine)—CH=N—N(indoline)  CH₃SO₄⁻;

(III7) H₃C—N⁺(pyridine)—CH=N—N(2,2,3,3-tetramethylindoline)  CH₃SO₄⁻;

(III8) H₃C—N⁺(pyridine)—CH=N—N(CH₃)(2-fluorophenyl)  Cl⁻;

(III9) H₃C—N⁺(pyridine)—CH=N—N(CH₃)(4-chlorophenyl)  Cl⁻;

(III10) (2-pyridinium, N-CH₃)—CH=N—N(CH₃)(phenyl)  CH₃SO₄⁻;

(III11) (2-pyridinium, N-CH₃)—CH=N—N(indoline)  CH₃SO₄⁻;

(III12) (2-pyridinium, N-CH₃)—CH=N—N(CH₃)(4-chlorophenyl)  CH₃SO₄⁻;

(III13) H₃C—N⁺(pyridine)—CH=N—N(CH₃)(C₆H₄—OCH₃)  CH₃SO₄⁻;

(III14) (1,3-dimethylimidazolium-2-yl)—N=N—(C₆H₄—OCH₃)  Cl⁻;

(III15) (2-pyridinium, N-CH₃)—CH=CH—(C₆H₄—NH₂)  CH₃COO⁻;

(III16) H₃C—N⁺(pyridine)—CH=CH—(C₆H₄—NH₂)  CH₃COO⁻;

(III17) H₃C—N⁺(pyridine)—CH=N—N(CH₃)(phenyl)  Cl⁻;  and (III18) 4-chlorophenyl—N=N—(6-hydroxy-1,2-dimethyl-indazolium-7-yl)  Cl⁻.

28. A composition according to claim 27, wherein the cationic direct dyes of formula (III) are chosen from the compounds having structures (III4), (III5) and (III13).

29. A composition according to claim 1, wherein the cationic direct dyes of formula (III') are chosen from the compounds corresponding to the following structures (III'1) to (III'3):

(III'1) (1-methylpyridinium-3-yl)—N=N—(2-methyl-1H-indol-3-yl)  Cl⁻;

(III'2) CH₃—N⁺(pyridine)—CH=CH—(1H-indol-3-yl)  Cl⁻;  and (III'3) (1,4-dimethyl-1,2,4-triazolium-5-yl)—N=N—(1-methyl-1H-indol-3-yl)  Cl⁻.

30. A composition according to claim 1, wherein the cationic direct dyes of formula (IV) are chosen from the compounds corresponding to the following structures (IV)1 to (IV)77:
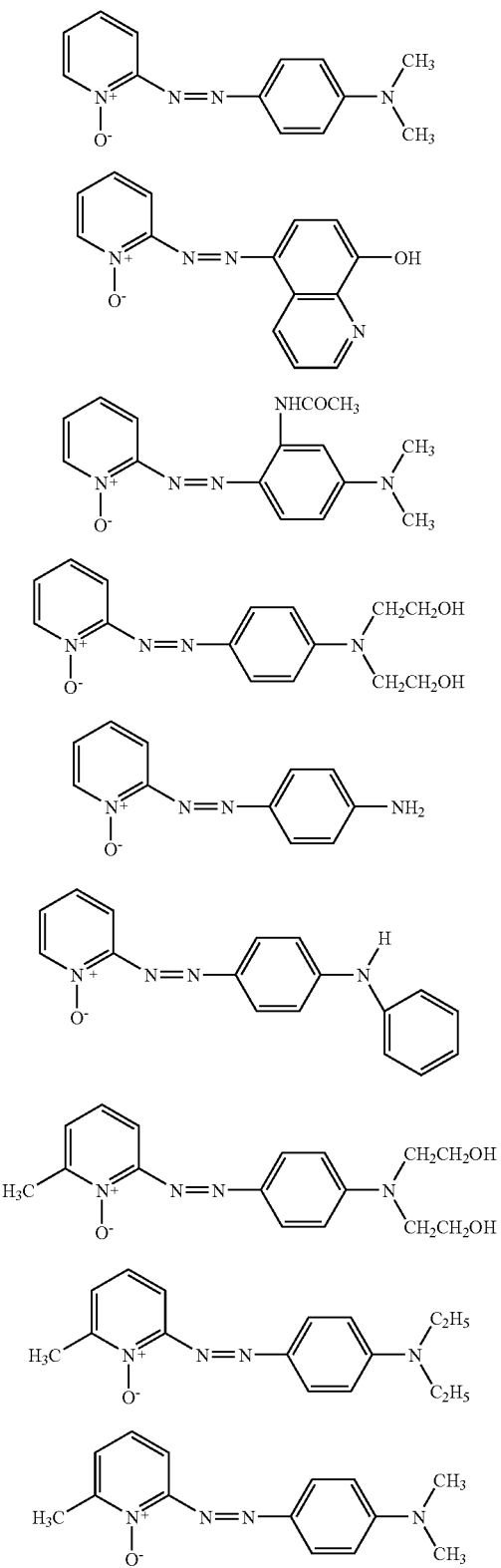
-continued
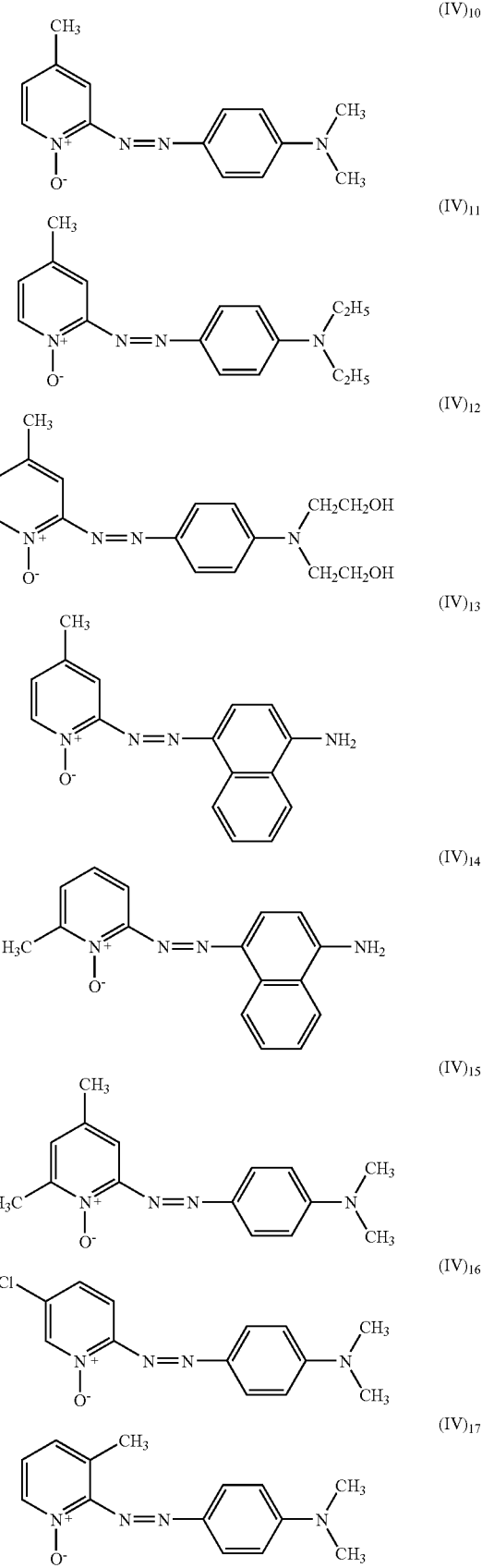

-continued
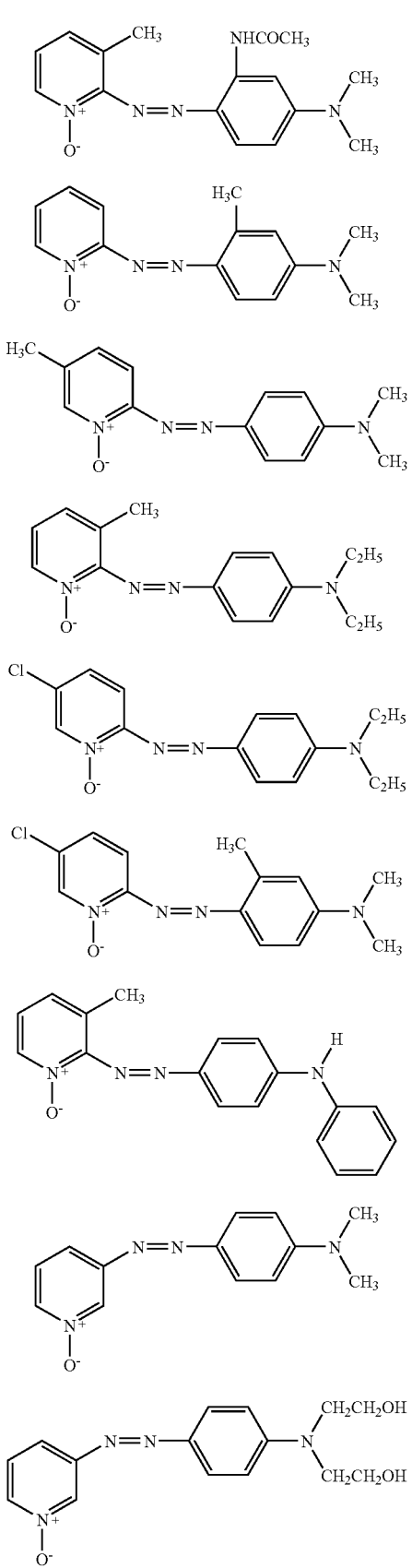
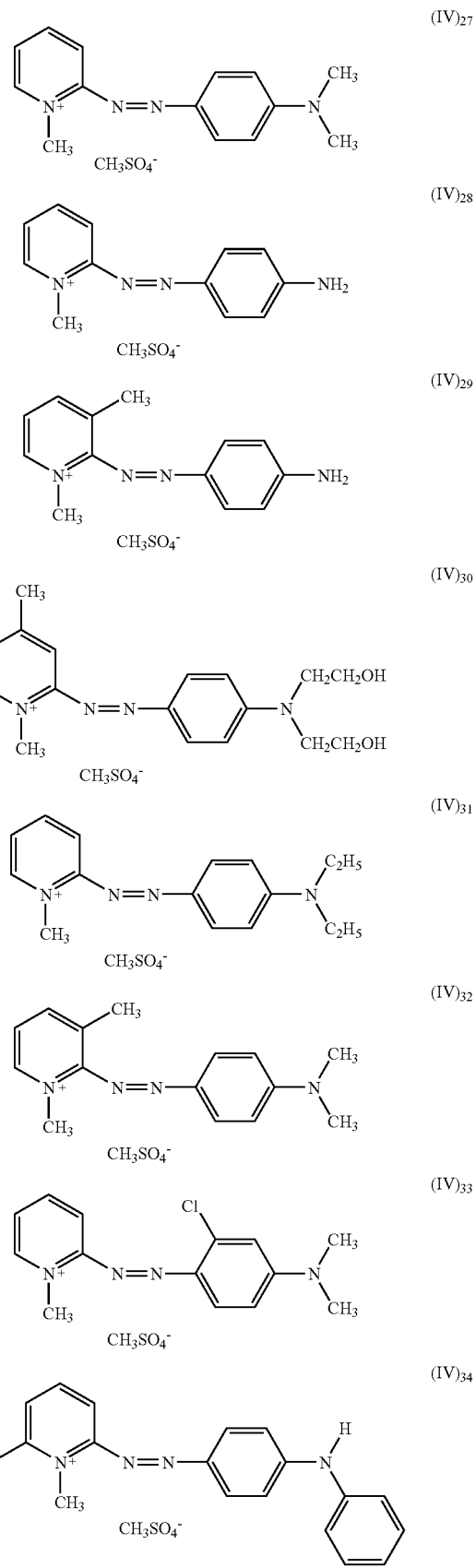

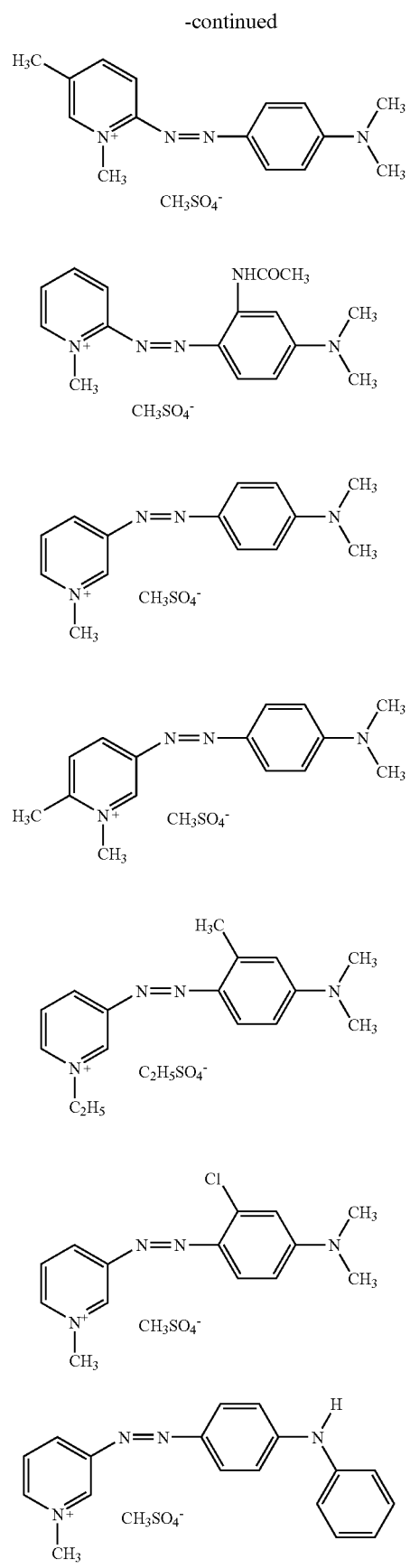
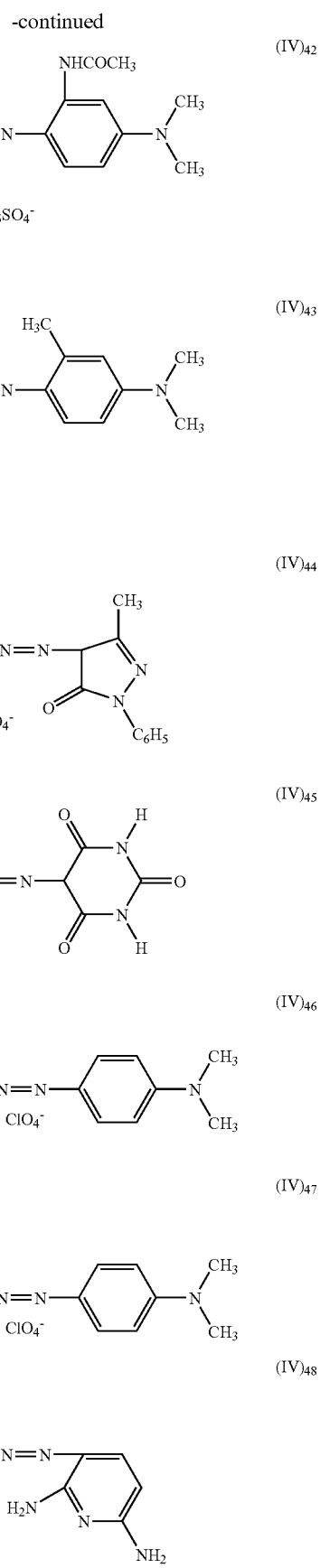

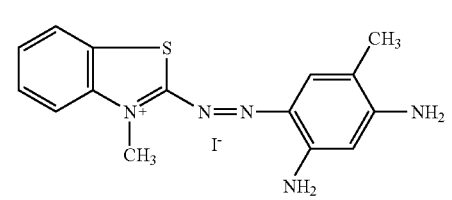
(IV)49
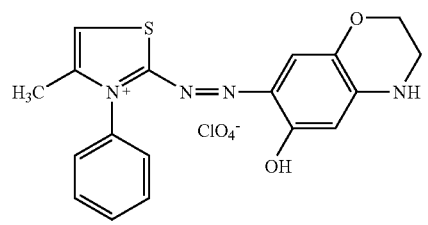
(IV)50
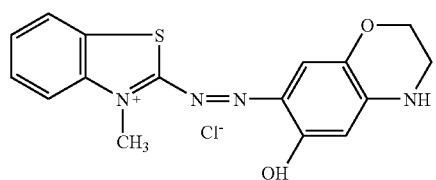
(IV)51
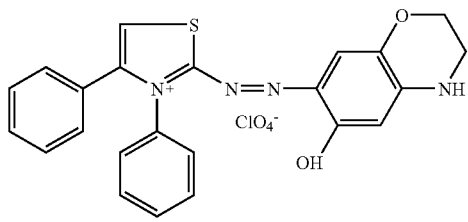
(IV)52
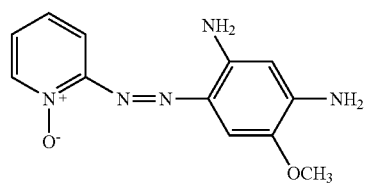
(IV)53
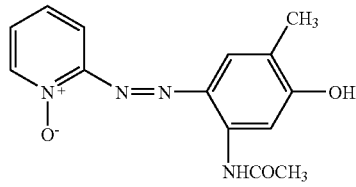
(IV)54
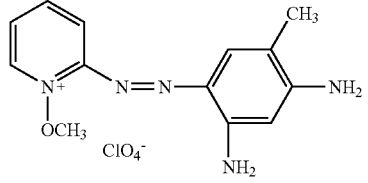
(IV)55
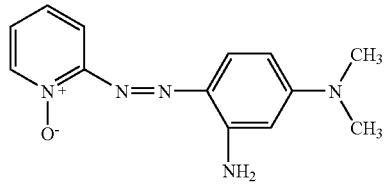
(IV)56
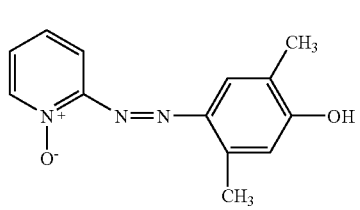
(IV)57
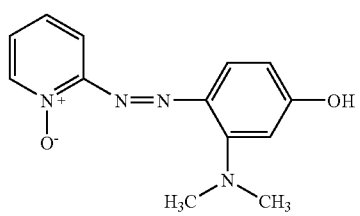
(IV)58
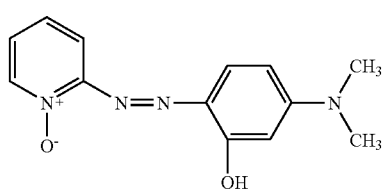
(IV)59
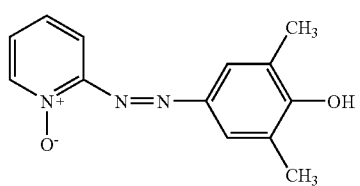
(IV)60
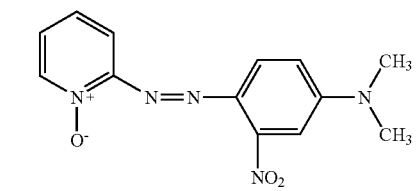
(IV)61
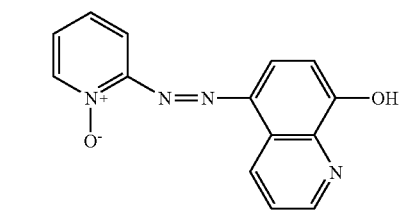
(IV)62
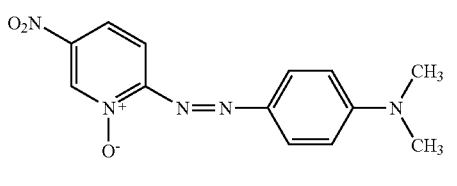
(IV)63
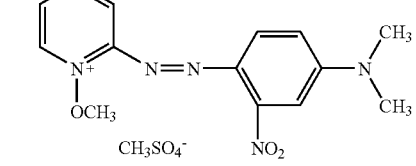
(IV)64

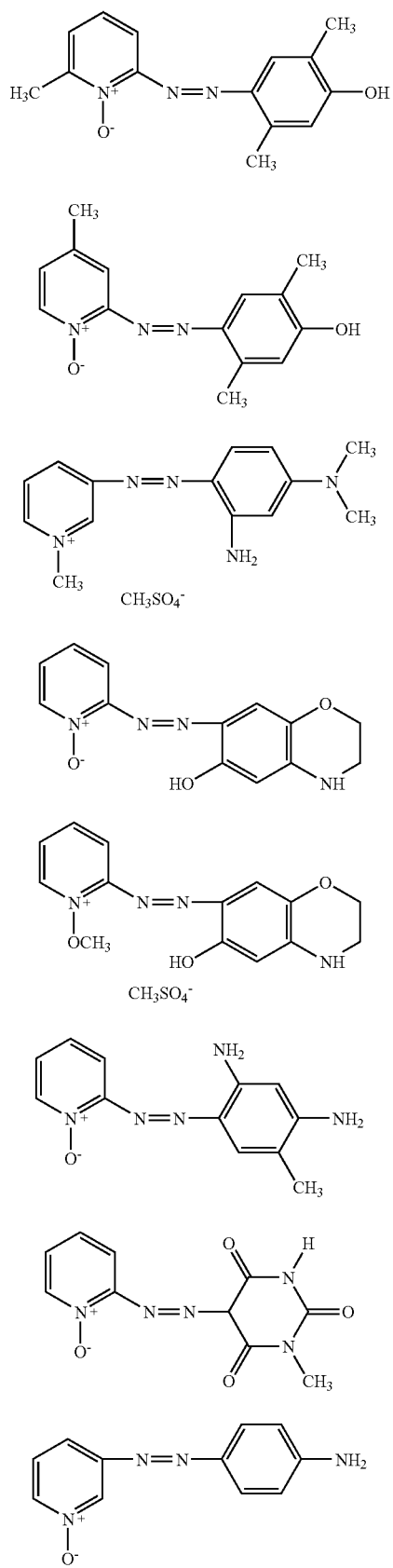
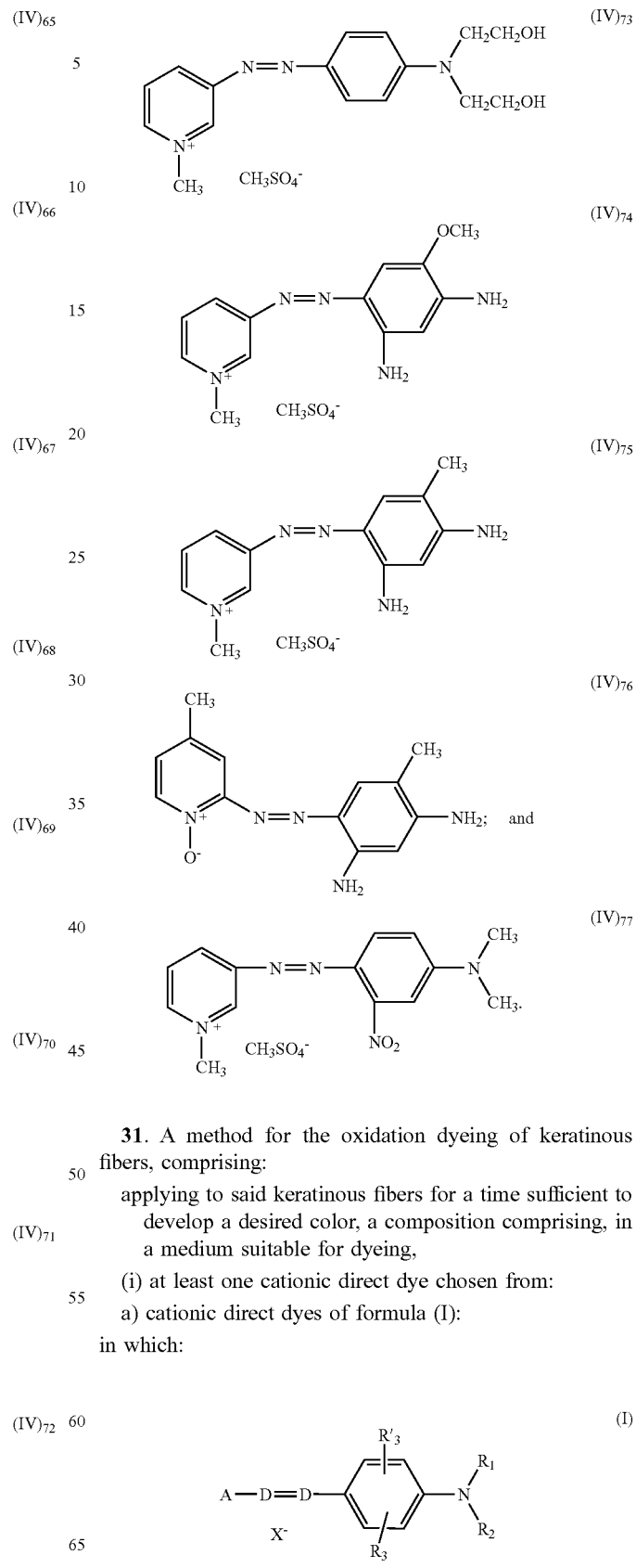
31. A method for the oxidation dyeing of keratinous fibers, comprising:
applying to said keratinous fibers for a time sufficient to develop a desired color, a composition comprising, in a medium suitable for dyeing,
(i) at least one cationic direct dye chosen from:
a) cationic direct dyes of formula (I):
in which:
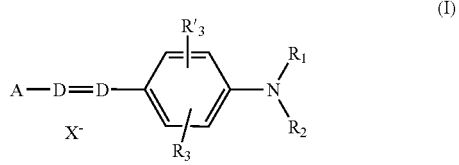

D is a nitrogen atom or a —CH group,

R₁ and R₂, which are identical or different, are chosen from a hydrogen atom; a C₁–C₄ alkyl radical which is unsubstituted or substituted with a —CN, —OH or —NH₂ radical or form with each other or a carbon atom of the benzene ring a heterocycle optionally containing at least one of oxygen and nitrogen and which is unsubstituted or substituted with at least one C₁–C₄ alkyl radical; and a 4'-aminophenyl radical, R₃ and R'₃, which are identical or different, are chosen from a hydrogen atom; a halogen atom chosen from chlorine, bromine, iodine and fluorine; a cyano radical; a C₁–C₄ alkyl radical; a C₁–C₄ alkoxy radical; and an acetyloxy radical, X⁻ is an anion, A is a group chosen from the following structures A₁ to A₁₉:

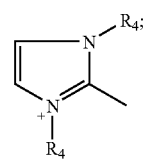 A₁

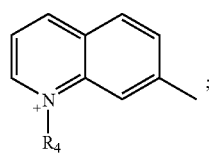 A₂

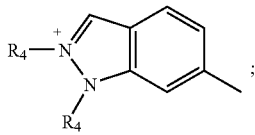 A₃

 A₄

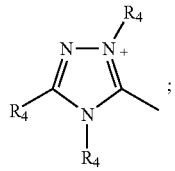 A₅

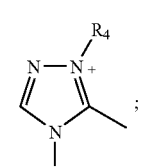 A₆

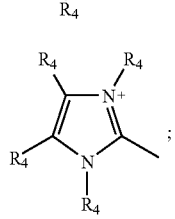 A₇

-continued

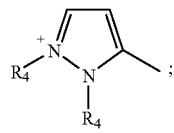 A₈

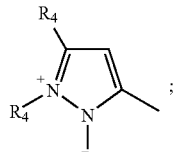 A₉

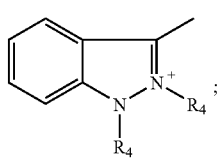 A₁₀

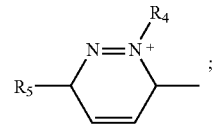 A₁₁

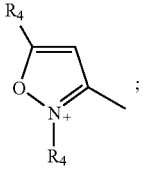 A₁₂

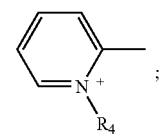 A₁₃

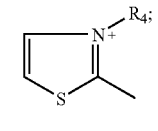 A₁₄

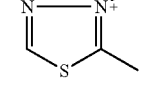 A₁₅

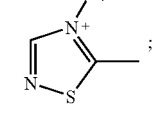 A₁₆

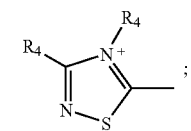 A₁₇

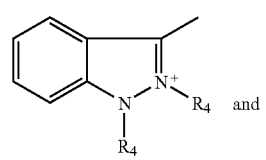 and A₁₈

-continued

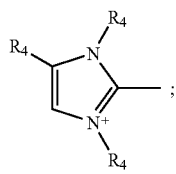
A19 in which $R_4$ is a $C_1$–$C_4$ alkyl radical which is unsubstituted or substituted with a hydroxyl radical and $R_5$ is a $C_1$–$C_4$ alkoxy radical, with the proviso that when 0 represents —CH, A is $A_4$ or $A_{13}$ and $R_3$ is different from an alkoxy radical, then $R_1$ and $R_2$ are not simultaneously hydrogen atoms;

b) cationic direct dyes of formula (II):

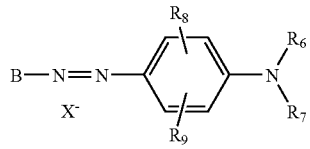
(II)

in which:

$R_6$ is a hydrogen atom or a $C_1$–$C_4$ alkyl radical, $R_7$ is chosen from a hydrogen atom; an alkyl radical which is unsubstituted or substituted with a —CN radical or with an amino group; and a 4'-aminophenyl radical, or forms with $R_6$ a heterocycle optionally containing at least one of oxygen and nitrogen and which is unsubstituted or substituted with a $C_1$–$C_4$ alkyl radical, $R_8$ and $R_9$, which are identical or different, are chosen from a hydrogen atom; a halogen atom chosen from bromine, chlorine, fluorine, and iodine; a $C_1$–$C_4$ alkyl radical; a $C_1$–$C_4$ alkoxy radical; and a —CN radical, $X^-$ is an anion, B represents a group chosen from the following structures B1 to B6:

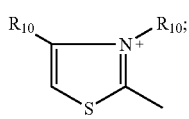
B1

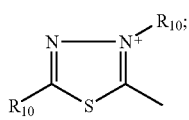
B2

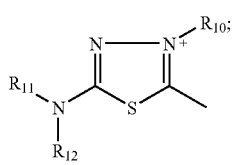
B3

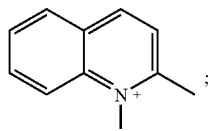
B4

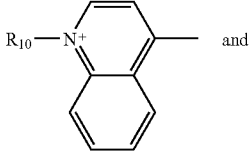
B5

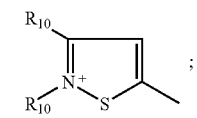
B6 in which $R_{10}$ is a $C_1$–$C_4$ alkyl radical, $R_{11}$ and $R_{12}$, which are identical or different, are a hydrogen atom or a $C_1$–$C_4$ alkyl radical;

c) cationic direct dyes of the following formula (III) and formula (III'):

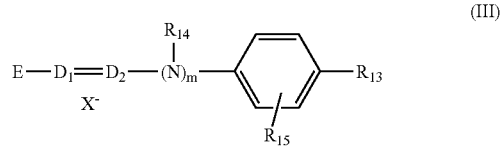
(III)

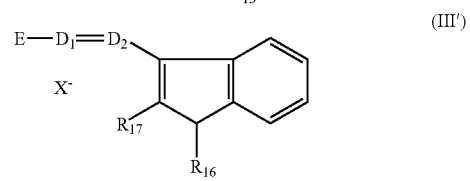
(III')

in which:

$R_{13}$ is chosen from a hydrogen atom, a $C_1$–$C_4$ alkoxy radical, a halogen atom chosen from bromine, chlorine, fluorine, and iodine; and an amino radical, $R_{14}$ is a hydrogen atom, a $C_1$–$C_4$ alkyl radical or forms with a carbon atom of the benzene ring a heterocycle which is optionally oxygen-containing and is unsubstituted or substituted with at least one $C_1$–$C_4$ alkyl group, $R_{15}$ is a hydrogen or halogen atom chosen from bromine, chlorine, fluorine, and iodine, $R_{16}$ and $R_{17}$, which are identical or different, are a hydrogen atom or a $C_1$–$C_4$ alkyl radical, $D_1$ and $D_2$, which are identical or different, are a nitrogen atom or a —CH group, m=0 or 1, with the proviso that when $R_{13}$ is an unsubstituted amino group, then $D_1$ and $D_2$ simultaneously are —CH groups and m=0, $X^-$ is an anion, E is a group chosen from the following structures E1 to E8:

E1 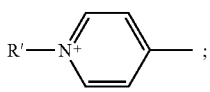

E2 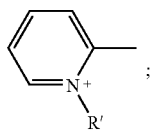

E3 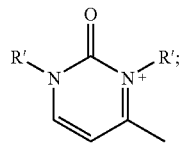

E4 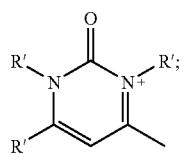

E5 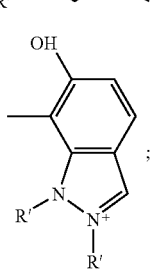

E6 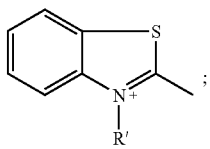

E7 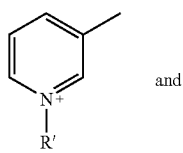 and

E8 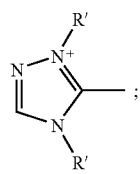

in which R' is a $C_1$–$C_4$ alkyl radical;

when m=0 and $D_1$ is a nitrogen atom, then E may also be a group having the following structure E9:

E9 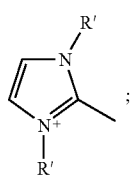

in which R' is a $C_1$–$C_4$ alkyl radical, and d) cationic direct dyes of formula (IV):

 (IV)

in which:
the symbol G is a group chosen from the following structures $G_1$ to $C_3$:

$G_1$ 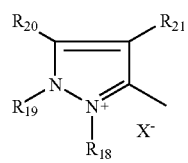

$G_2$ 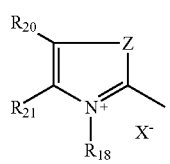

$G_3$ 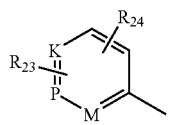

in which structures $G_1$ to $G_3$, $R_{18}$ is chosen from a $C_1$–$C_4$ alkyl radical; a phenyl radical which is unsubstituted or substituted with a $C_1$–$C_4$ alkyl radical or with a halogen atom chosen from chlorine, bromine, iodine and fluorine;

$R_{19}$ is a $C_1$–$C_4$ alkyl radical or a phenyl radical;

$R_{20}$ and $R_{21}$, which are identical or different, are chosen from a $C_1$–$C_4$ alkyl radical and a phenyl radical, or form together in $G_1$ a benzene ring which is substituted with at least one radical chosen from $C_1$–$C_4$ alkyl, $C_1$–$C_4$ alkoxy and $NO_2$ radicals, or form together in $G_2$ a benzene ring which is optionally substituted with at least one radical chosen from $C_1$–$C_4$ alkyl, $C_1$–$C_4$ alkoxy and $NO_2$ radicals;

$R_{20}$ may also be a hydrogen atom;

Z is an oxygen or sulphur atom or an —$NR_{19}$ group;

M is a group chosen from —CH; —CR wherein R is $C_1$–$C_4$ alkyl; and —$NR_{22}(X^-)_r$;

K is a group chosen from —CH; —CR wherein R is $C_1$–$C_4$ alkyl; and —$NR_{22}(X^-)_r$;

P is a group chosen from —CH; —CR wherein R denotes $C_1$–$C_4$ alkyl; and —$NR_{22}(X^-)_r$ where r is zero or 1;

$R_{22}$ is chosen from an 0 atom, a $C_1$–$C_4$ alkoxy radical and a $C_1$–$C_4$ alkyl radical;

$R_{23}$ and $R_{24}$, which are identical or different, are chosen from a hydrogen atom; a halogen atom chosen from chlorine, bromine, iodine and fluorine; a $C_1$–$C_4$ alkyl radical;

H a $C_1$–$C_4$ alkoxy radical; and an —$NO_2$ radical;

$X^-$ is an anion;

wherein J is chosen from:

(a) a group having the following structure $J_1$:

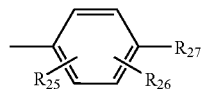

in which structure $J_1$, $R_{25}$ is chosen from a hydrogen atom; a halogen atom chosen from chlorine, bromine, iodine and fluorine; a $C_1$–$C_4$ alkyl radical; a $C_1$–$C_4$ alkoxy radical; and a radical chosen from —OH, —$NO_2$, —$NHR_{28}$, —$NR_{29}R_{30}$, and —NHCO($C_1$–$C_4$alkyl), or forms with $R_{26}$ a 5- or 6-membered ring optionally containing at least one heteroatom chosen from nitrogen, oxygen and sulphur;

$R_{26}$ is chosen from a hydrogen atom; a halogen atom chosen from chlorine, bromine, iodine and fluorine; a $C_1$–$C_4$ alkyl radical; and a $C_1$–$C_4$ alkoxy radical, or forms with $R_{27}$ or $R_{28}$ a 5- or 6-membered ring optionally containing at least one heteroatom chosen from nitrogen, oxygen or sulphur;

$R_{27}$ is chosen from a hydrogen atom, an —OH radical, an —$NHR_{28}$ radical, and an —$NR_{29}R_{30}$ radical;

$R_{28}$ is chosen from a hydrogen atom, a $C_1$–$C_4$ alkyl radical, a $C_1$–$C_4$ monohydroxyalkyl radical, a $C_2$–$C_4$ polyhydroxyalkyl radical, and a phenyl radical;

$R_{29}$ and $R_{30}$, which are identical or different, are chosen from a $C_1$–$C_4$ alkyl radical, a $C_1$–$C_4$ monohydroxyalkyl radical, and a $C_2$–$C_4$ polyhydroxyalkyl radical; and (b) a 5- or 6-membered nitrogen-containing heterocycle group which optionally contains additional heteroatoms, carbonyl-containing groups, or a mixture of additional heteroatoms and carbonyl-containing groups and which is unsubstituted or substituted with at least one radical chosen from $C_1$–$C_4$ alkyl, amino and phenyl radicals, (ii) at least one quaternary ammonium salt chosen from:

$(ii)_1$—quaternary ammonium salts of the following formula (V):

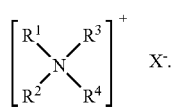

in which the radicals $R^1$ $R^2$, $R^3$, and $R^4$, which are identical or different, are chosen from a saturated or unsaturated, linear or branched, aliphatic hydrocarbon radical comprising 1 to 30 carbon atoms; and a radical chosen from alkoxy, alkoxycarbonylalkyl, polyoxyalkylene, alkylamido, alkylamidoalkyl, hydroxyalkyl, aromatic, aryl and alkylaryl radicals comprising 12 to 30 carbon atoms, wherein at least one radical among $R^1$, $R^2$, $R^3$ and $R^4$ is a radical comprising 8 to 30 carbon atoms;

$X^-$ is an anion chosen from halides, phosphates, acetates, lactates and alkyl sulphates;

$(ii)_2$—imidazolium salts of the following formula (VI):

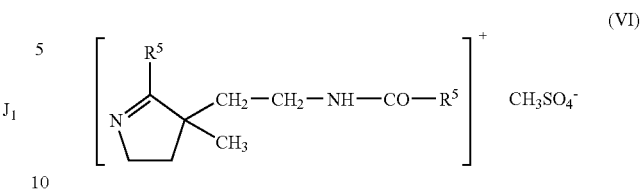

in which $R^5$ is chosen from alkenyl radicals and alkyl radicals, said alkenyl radicals and alkyl radicals comprising 13 to 31 carbon atoms and being derived from tallow fatty acids;

$(ii)_3$—quaternary diammonium salts of the following formula (VII):

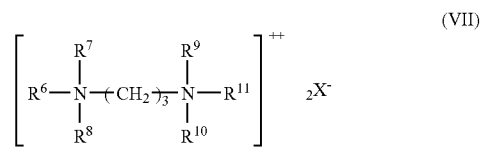

in which $R^6$ is an aliphatic radical comprising 16 to 30 carbon atoms, $R^7$, $R^8$, $R^9$, $R^{10}$ and $R^{11}$ are chosen from hydrogen or an alkyl radical comprising 1 to 4 carbon atoms, and $X^-$ is an anion chosen from halides, acetates, phosphates and sulphates, and (iii) at least one oxidation base.

32. A method according to claim 31, further comprising rinsing said keratinous fibers after applying said composition thereon.

33. A method according to claim 32, further comprising washing said keratinous fibers with shampoo after said rinsing;

and rinsing again said keratinous fibers after said washing.

34. A method according to claim 33, further comprising, after said washing and rinsing, drying said keratinous fibers.

35. A method according to claim 31, wherein said keratinous fibers are human keratinous fibers.

36. A method according to claim 35, wherein said human keratinous fibers are hair.

37. A composition for the oxidation dyeing of keratinous fibers, comprising (i) a cationic direct dye of structure (I1):

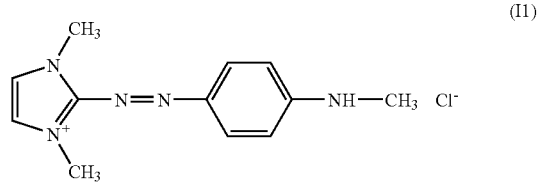

(ii) oleocetyldimethylhydroxyethylammoniuim chloride; and (iii) at least one oxidation base.

38. A composition for the oxidation dyeing of keratinous fibers, comprising:

(i) a cationic direct dye of structure (I14):

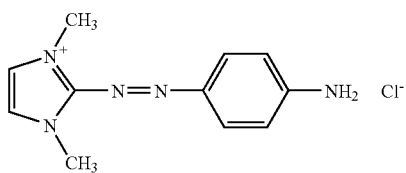

(ii) behenyltrimethylammonium chloride; and
(iii) at least one oxidation base.

39. A composition for the oxidation dyeing of keratinous fibers, comprising:
(i) a cationic direct dye of structure $(IV)_{27}$:

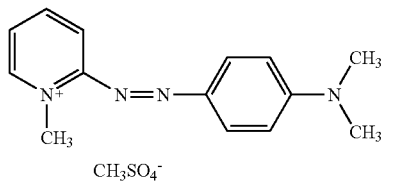

(ii) cetyltrimethylammonium chloride; and
(iii) at least one oxidation base.

40. A method for the oxidation dyeing of keratinous fibers, comprising
separately storing a first composition and a second composition;
mixing said first composition with said second composition before applying the resultant mixture to said keratinous fibers; and
applying said mixture to the keratinous fibers,
wherein said first composition comprises, in a medium suitable for dyeing:
(i) at least one oxidation base; and
(ii) at least one cationic direct dye chosen from:
a) cationic direct dyes of formula (I):

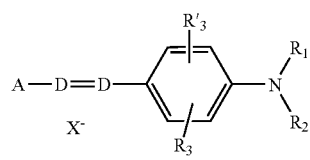

in which:
D is a nitrogen atom or a —CH group,
$R_1$ and $R_2$, which are identical or different, are chosen from a hydrogen atom; a $C_1$–$C_4$ alkyl radical which is unsubstituted or substituted with a —CN, —OH or —$NH_2$ radical or form with each other or a carbon atom of the benzene ring a heterocycle optionally containing at least one of oxygen and nitrogen and which is unsubstituted or substituted with at least one $C_1$–$C_4$ alkyl radical; and a 4′-aminophenyl radical,
$R_3$ and $R'_3$, which are identical or different, are chosen from a hydrogen atom; a halogen atom chosen from chlorine, bromine, iodine and fluorine; a cyano radical; a $C_1$–$C_4$ alkyl radical; a $C_1$–$C_4$ alkoxy radical; and an acetyloxy radical, $X^-$ is an anion, A is a group chosen from the following structures $A_1$ to $A_{19}$:

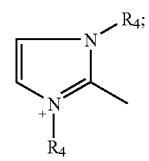
$A_1$

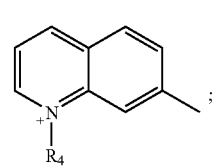
$A_2$

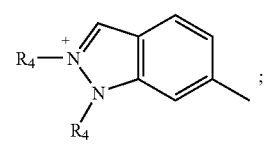
$A_3$

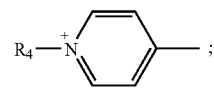
$A_4$

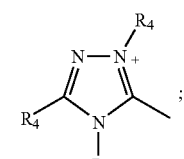
$A_5$

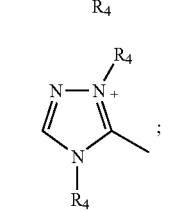
$A_6$

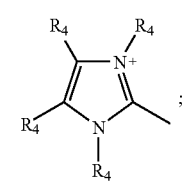
$A_7$

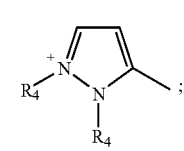
$A_8$

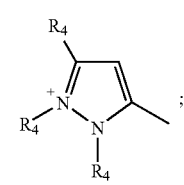
$A_9$

-continued

A10 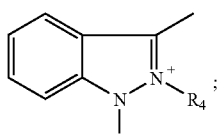

A11 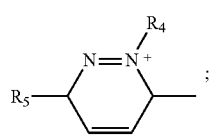

A12 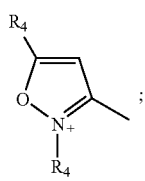

A13 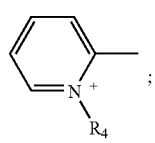

A14 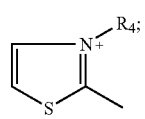

A15 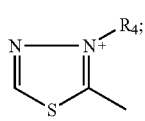

A16 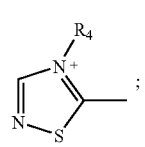

A17 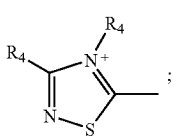

A18 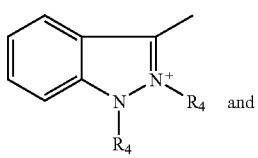 and

A19 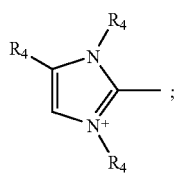

in which $R_4$ is a $C_1$–$C_4$ alkyl radical which is unsubstituted or substituted with a hydroxyl radical and $R_5$ is a $C_1$–$C_4$ alkoxy radical, with the proviso that when D represents —CH, A is $A_4$ or $A_{13}$ and $R_3$ is different from an alkoxy radical, then $R_1$ and $R_2$ are not simultaneously hydrogen atoms;

b) cationic direct dyes of formula (II):

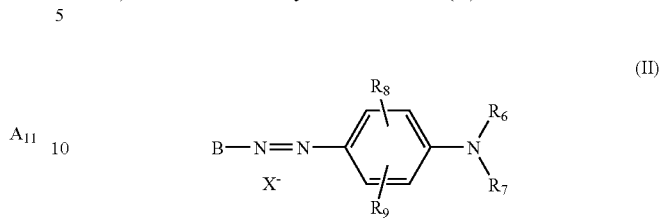

(II)

in which:
$R_6$ is a hydrogen atom or a $C_1$–$C_4$ alkyl radical,
$R_7$ is chosen from a hydrogen atom; an alkyl radical which is unsubstituted or substituted with a —CN radical or with an amino group; and a 4'-aminophenyl radical, or forms with $R_6$ a heterocycle optionally containing at least one of oxygen and nitrogen and which is unsubstituted or substituted with a $C_1$–$C_4$ alkyl radical,
$R_8$ and $R_9$, which are identical or different, are chosen from a hydrogen atom; a halogen atom chosen from bromine, chlorine, fluorine, and iodine; a $C_1$–$C_4$ alkyl radical; a $C_1$–$C_4$ alkoxy radical; and a —CN radical,
$X^-$ is an anion,
B represents a group chosen from the following structures B1 to B6:

B1 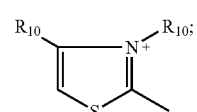

B2 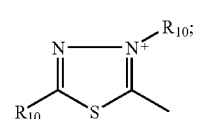

B3 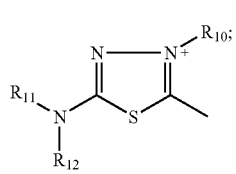

B4 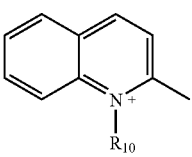

B5 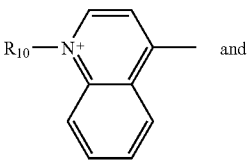 and

B6 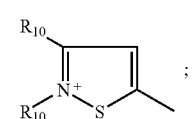

in which $R_{10}$ is a $C_1$–$C_4$ alkyl radical, $R_{11}$ and $R_{12}$, which are identical or different, are a hydrogen atom or a $C_1$–$C_4$ alkyl radical;

c) cationic direct dyes of the following formula (III) and formula (III'):

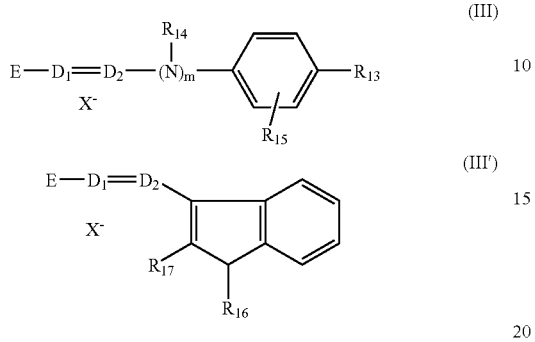

in which:
- $R_{13}$ is chosen from a hydrogen atom, a $C_1$–$C_4$ alkoxy radical, a halogen atom chosen from bromine, chlorine, fluorine, and iodine; and an amino radical,
- $R_{14}$ is a hydrogen atom, a $C_1$–$C_4$ alkyl radical or forms with a carbon atom of the benzene ring a heterocycle which is optionally oxygen-containing and is unsubstituted or substituted with at least one $C_1$–$C_4$ alkyl group,
- $R_{15}$ is a hydrogen or halogen atom chosen from bromine, chlorine, fluorine, and iodine,
- $R_{16}$ and $R_{17}$, which are identical or different, are a hydrogen atom or a $C_1$–$C_4$ alkyl radical,
- $D_1$ and $D_2$, which are identical or different, are a nitrogen atom or a —CH group,
- m=0 or 1, with the proviso that when $R_{13}$ is an unsubstituted amino group, then $D_1$ and $D_2$ simultaneously are —CH groups and m=0;

$X^-$ is an anion,

E is a group chosen from the following structures E1 to E8:

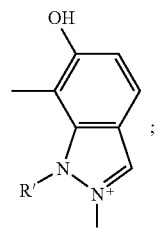

E1

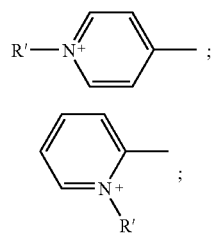

E2

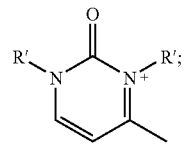

E3

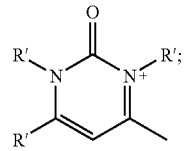

E4

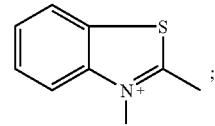

E5

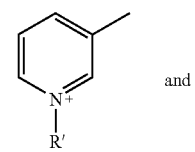

E6

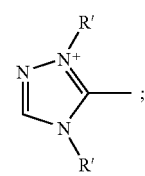

E7 and

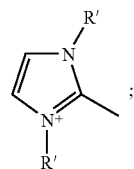

E8 in which R' is a $C_1$–$C_4$ alkyl radical;

when m=0 and $D_1$ is a nitrogen atom, then E may also be a group having the following structure E9:

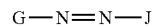

E9 in which R' is a $C_1$–$C_4$ alkyl radical, and d) cationic direct dyes of formula (IV):

$$G-N=N-J \qquad (IV)$$

in which:
the symbol G is a group chosen from the following structures $G_1$ to $G_3$:

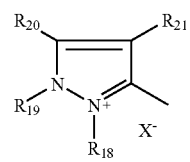

$G_1$

-continued

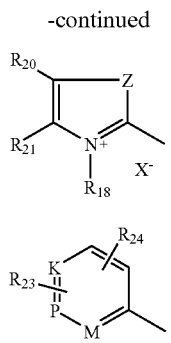

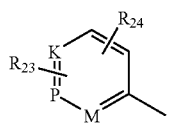

in which structures $G_1$ to $G_3$,
- $R_{18}$ is chosen from a $C_1$–$C_4$ alkyl radical; a phenyl radical which is unsubstituted or substituted with a $C_1$–$C_4$ alkyl radical or with a halogen atom chosen from chlorine, bromine, iodine and fluorine;
- $R_{19}$ is a $C_1$–$C_4$ alkyl radical or a phenyl radical;
- $R_{20}$ and $R_{21}$, which are identical or different, are chosen from a $C_1$–$C_4$ alkyl radical and a phenyl radical, or form together in $G_1$ a benzene ring which is substituted with at least one radical chosen from $C_1$–$C_4$ alkyl, $C_1$–$C_4$ alkoxy and $NO_2$ radicals, or form together in $G_2$ a benzene ring which is optionally substituted with at least one radical chosen from $C_1$–$C_4$ alkyl, $C_1$–$C_4$ alkoxy and $NO_2$ radicals;
- $R_{20}$ may also be a hydrogen atom;
- Z is an oxygen or sulphur atom or an —$NR_{19}$ group;
- M is a group chosen from —CH; —CR wherein R is $C_1$–$C_4$ alkyl; and —$NR_{22}(X^-)_r$;
- K is a group chosen from —CH; —CR wherein R is $C_1$–$C_4$ alkyl; and —$NR_{22}(X^-)_r$;
- P is a group chosen from —CH; —CR wherein R denotes $C_1$–$C_4$ alkyl; and —$NR_{22}(X^-)_r$ where r is zero or 1;
- $R_{22}$ is chosen from an $O^-$ atom, a $C_1$–$C_4$ alkoxy radical and a $C_1$–$C_4$ alkyl radical;
- $R_{23}$ and $R_{24}$, which are identical or different, are chosen from a hydrogen atom; a halogen atom chosen from chlorine, bromine, iodine and fluorine; a $C_1$–$C_4$ alkyl radical; a $C_1$–$C_4$ alkoxy radical; and an —$NO_2$ radical;
- $X^-$ is an anion;
  wherein J is chosen from:
  (a) a group having the following structure $J_1$:

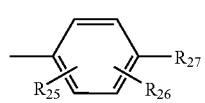

in which structure $J_1$,
- $R_{25}$ is chosen from a hydrogen atom; a halogen atom chosen from chlorine, bromine, iodine and fluorine; a $C_1$–$C_4$ alkyl radical; a $C_1$–$C_4$ alkoxy radical; and a radical chosen from —OH, —$NO_2$, —$NHR_{25}$, —$NR_{29}R_{30}$, and —NHCO($C_1$–$C_4$alkyl), or forms with $R_{26}$ a 5- or 6-membered ring optionally containing at least one heteroatom chosen from nitrogen, oxygen and sulphur;
- $R_{26}$ is chosen from a hydrogen atom; a halogen atom chosen from chlorine, bromine, iodine and fluorine; a $C_1$–$C_4$ alkyl radical; and a $C_1$–$C_4$ alkoxy radical, or forms with $R_{27}$ or $R_{28}$ a 5- or 6-membered ring optionally containing at least one heteroatom chosen from nitrogen, oxygen or sulphur;
- $R_{27}$ is chosen from a hydrogen atom, an —OH radical, an —$NHR_{28}$ radical, and an —$NR_{29}R_{30}$ radical;
- $R_{28}$ is chosen from a hydrogen atom, a $C_1$–$C_4$ alkyl radical, a $C_1$–$C_4$ monohydroxyalkyl radical, a $C_2$–$C_4$ polyhydroxyalkyl radical, and a phenyl radical;
- $R_{29}$ and $R_{30}$, which are identical or different, are chosen from a $C_1$–$C_4$ alkyl radical, a $C_1$–$C_4$ monohydroxyalkyl radical, and a $C_2$–$C_4$ polyhydroxyalkyl radical; and (b) a 5- or 6-membered nitrogen-containing heterocycle group which optionally contains additional heteroatoms, carbonyl-containing groups, or a mixture of additional heteroatoms and carbonyl-containing groups and which is unsubstituted or substituted with at least one radical chosen from $C_1$–$C_4$ alkyl, amino and phenyl radicals, and wherein said second composition comprises, in a medium suitable for dyeing, at least one oxidizing agent; and wherein either said first composition or said second composition further comprises at least one quaternary ammonium salt chosen from:

(ii)$_1$—quaternary ammonium salts of the following formula (V):

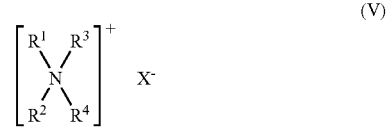

in which
- the radicals $R^1$ $R^2$, $R^3$, and $R^4$, which are identical or different, are chosen from a saturated or unsaturated, linear or branched, aliphatic hydrocarbon radical comprising 1 to 30 carbon atoms; and a radical chosen from alkoxy, alkoxycarbonylalkyl, polyoxyalkylene, alkylamido, alkylamidoalkyl, hydroxyalkyl, aromatic, aryl and alkylaryl radicals comprising 12 to 30 carbon atoms, wherein at least one radical among $R^1$, $R^2$, $R^3$ and $R^4$ is a radical comprising 8 to 30 carbon atoms;
- $X^-$ is an anion chosen from halides, phosphates, acetates, lactates and alkyl sulphates;

(ii)$_2$—imidazolium salts of the following formula (VI):

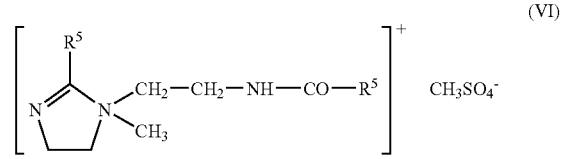

in which
- $R^5$ is chosen from alkenyl radicals and alkyl radicals, said alkenyl radicals and alkyl radicals comprising 13 to 31 carbon atoms and being derived from tallow fatty acids;

(ii)$_3$—quaternary diammonium salts of the following formula (VII):

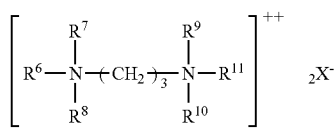
(VII)

in which
- $R^6$ is an aliphatic radical comprising 16 to 30 carbon atoms,
- $R^7$, $R^8$, $R^9$, $R^{10}$ and $R^{11}$ are chosen from hydrogen or an alkyl radical comprising 1 to 4 carbon atoms, and $X^-$ is an anion chosen from halides, acetates, phosphates and sulphates.

41. A method according to claim 40, wherein said keratinous fibers are human keratinous fibers.

42. A method according to claim 41, wherein said human keratinous fibers are hair.

43. A multicompartment oxidation dyeing kit wherein a first compartment contains a first composition and a second compartment contains a second composition, wherein said first composition comprises, in a medium suitable for dyeing:
(i) at least one oxidation base; and
(ii) at least one cationic direct dye chosen from:
a) cationic direct dyes of formula (I):

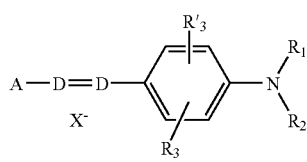
(I)

in which:
- D is a nitrogen atom or a —CH group,
- $R_1$ and $R_2$, which are identical or different, are chosen from a hydrogen atom; a $C_1$–$C_4$ alkyl radical which is unsubstituted or substituted with a —CN, —OH or —$NH_2$ radical or form with each other or a carbon atom of the benzene ring a heterocycle optionally containing at least one of oxygen and nitrogen and which is unsubstituted or substituted with at least one $C_1$–$C_4$ alkyl radical; and a 4'-aminophenyl radical,
- $R_3$ and $R'_3$, which are identical or different, are chosen from a hydrogen atom; a halogen atom chosen from chlorine, bromine, iodine and fluorine; a cyano radical; a $C_1$–$C_4$ alkyl radical; a $C_1$–$C_4$ alkoxy radical; and an acetyloxy radical,
- $X^-$ is an anion,
- A is a group chosen from the following structures $A_1$ to $A_{19}$:

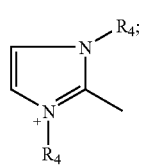
$A_1$

-continued

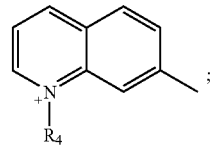
$A_2$

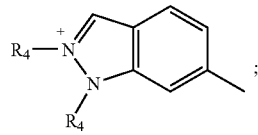
$A_3$

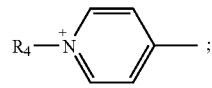
$A_4$

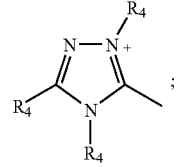
$A_5$

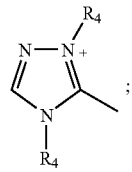
$A_6$

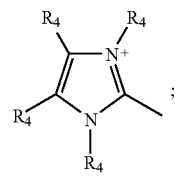
$A_7$

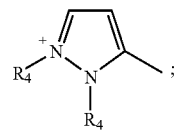
$A_8$

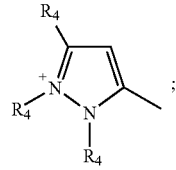
$A_9$

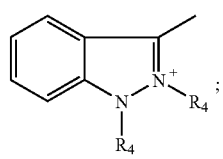
$A_{10}$

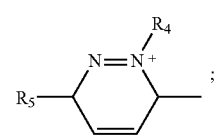
$A_{11}$

-continued

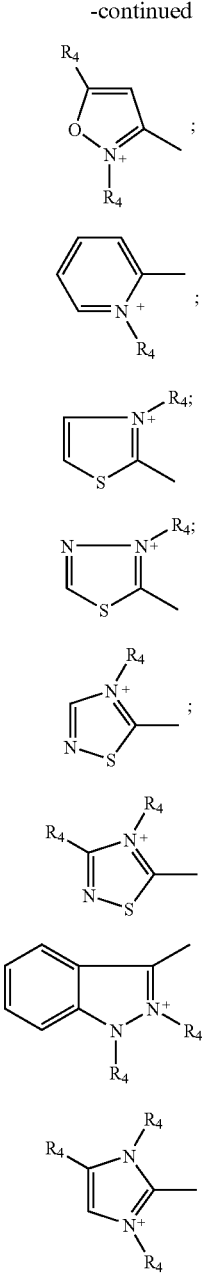

A₁₂

A₁₃

A₁₄

A₁₅

A₁₆

A₁₇

A₁₈ and

A₁₉ in which R₄ is a C₁–C₄ alkyl radical which is unsubstituted or substituted with a hydroxyl radical and R₅ is a C₁–C₄ alkoxy radical, with the proviso that when D represents —CH, A is A₄ or A₁₃ and R₃ is different from an alkoxy radical, then R₁ and R₂ are not simultaneously hydrogen atoms;

b) cationic direct dyes of formula (II):

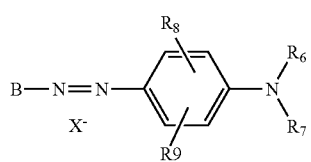

(II)

in which:

R₆ is a hydrogen atom or a C₁–C₄ alkyl radical,

R₇ is chosen from a hydrogen atom; an alkyl radical which is unsubstituted or substituted with a —CN radical or with an amino group; and a 4'-aminophenyl radical, or forms with R₆ a heterocycle optionally containing at least one of oxygen and nitrogen and which is unsubstituted or substituted with a C₁–C₄ alkyl radical, R₈ and R₉, which are identical or different, are chosen from a hydrogen atom; a halogen atom chosen from bromine, chlorine, fluorine, and iodine; a C₁–C₄ alkyl radical; a C₁–C₄ alkoxy radical; and a —CN radical, X⁻ is an anion, B represents a group chosen from the following structures B1 to B6:

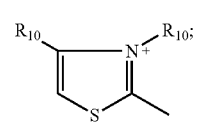

B1

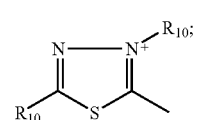

B2

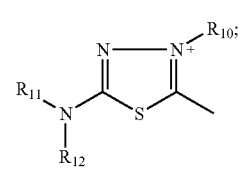

B3

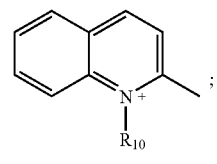

B4

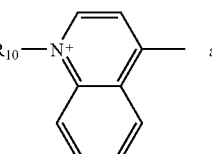

B5

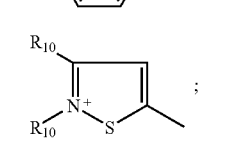

B6 in which R₁₀ is a C₁–C₄ alkyl radical, R₁₁ and R₁₂, which are identical or different, are a hydrogen atom or a C₁–C₄ alkyl radical;

c) cationic direct dyes of the following formula (III) and formula (III'):

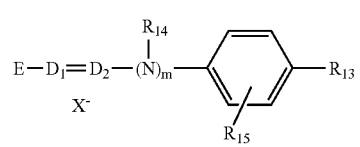

(III)

-continued

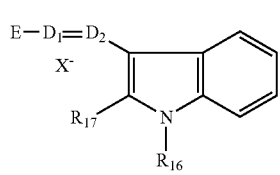
(III')

in which:
- R$_{13}$ is chosen from a hydrogen atom, a C$_1$–C$_4$ alkoxy radical, a halogen atom chosen from bromine, chlorine, fluorine, and iodine; and an amino radical,
- R$_{14}$ is a hydrogen atom, a C$_1$–C$_4$ alkyl radical or forms with a carbon atom of the benzene ring a heterocycle which is optionally oxygen-containing and is unsubstituted or substituted with at least one C$_1$–C$_4$ alkyl group,
- R$_{15}$ is a hydrogen or halogen atom chosen from bromine, chlorine, fluorine, and iodine,
- R$_{16}$ and R$_{17}$, which are identical or different, are a hydrogen atom or a C$_1$–C$_4$ alkyl radical,
- D$_1$ and D$_2$, which are identical or different, are a nitrogen atom or a —CH group,
- m=0 or 1, with the proviso that when R$_{13}$ is an unsubstituted amino group, then D$_1$ and D$_2$ simultaneously are —CH groups and m=0, X$^-$ is an anion, E is a group chosen from the following structures E1 to E8:

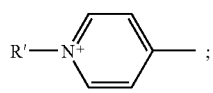
E1

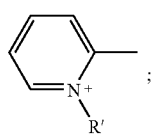
E2

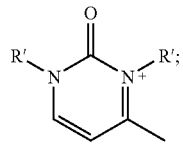
E3

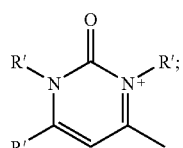
E4

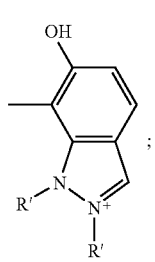
E5

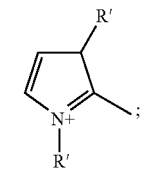
E6

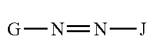
E7
and

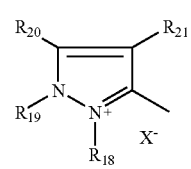
E8 in which R' is a C$_1$–C$_4$ alkyl radical;
when m=0 and D$_1$ is a nitrogen atom, then E may also be a group having the following structure E9:

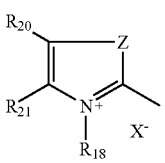
E9 in which R' is a C$_1$–C$_4$ alkyl radical, and d) cationic direct dyes of formula (IV):

$$G-N=N-J$$ (IV)

in which:
the symbol G is a group chosen from the following structures G$_1$ to G$_3$:

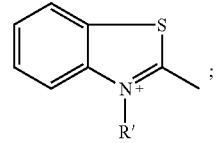
G$_1$

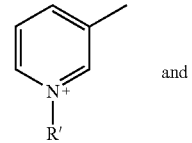
G$_2$

-continued

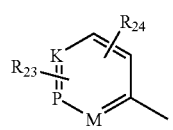

in which structures $G_1$ to $G_3$,
- $R_{18}$ is chosen from a $C_1$–$C_4$ alkyl radical; a phenyl radical which is unsubstituted or substituted with a $C_1$–$C_4$ alkyl radical or with a halogen atom chosen from chlorine, bromine, iodine and fluorine;
- $R_{19}$ is a $C_1$–$C_4$ alkyl radical or a phenyl radical;
- $R_{20}$ and $R_{21}$, which are identical or different, are chosen from a $C_1$–$C_4$ alkyl radical and a phenyl radical, or form together in $G_1$ a benzene ring which is substituted with at least one radical chosen from $C_1$–$C_4$ alkyl, $C_1$–$C_4$ alkoxy and $NO_2$ radicals, or form together in $G_2$ a benzene ring which is optionally substituted with at least one radical chosen from $C_1$–$C_4$ alkyl, $C_1$–$C_4$ alkoxy and $NO_2$ radicals;
- $R_{20}$ may also be a hydrogen atom;
- Z is an oxygen or sulphur atom or an —$NR_{19}$ group;
- M is a group chosen from —CH; —CR wherein R is $C_1$–$C_4$ alkyl; and —$NR_{22}(X^-)_r$;
- K is a group chosen from —CH; —CR wherein R is $C_1$–$C_4$ alkyl; and —$NR_{22}(X^-)_r$;
- P is a group chosen from —CH; —CR wherein R denotes $C_1$–$C_4$ alkyl; and —$NR_{22}(X^-)_r$ where r is zero or 1;
- $R_{22}$ is chosen from an $O^-$ atom, a $C_1$–$C_4$ alkoxy radical and a $C_1$–$C_4$ alkyl radical;
- $R_{23}$ and $R_{24}$, which are identical or different, are chosen from a hydrogen atom; a halogen atom chosen from chlorine, bromine, iodine and fluorine; a $C_1$–$C_4$ alkyl radical; a $C_1$–$C_4$ alkoxy radical; and an —$NO_2$ radical;
- $X^-$ is an anion;

wherein J is chosen from:
(a) a group having the following structure $J_1$:

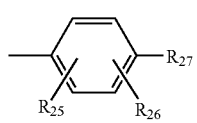

in which structure $J_1$,
- $R_{25}$ is chosen from a hydrogen atom; a halogen atom chosen from chlorine, bromine, iodine and fluorine; a $C_1$–$C_4$ alkyl radical; a $C_1$–$C_4$ alkoxy radical; and a radical chosen from —OH, —$NO_2$, —$NHR_{28}$, —$NR_{29}R_{30}$, and —$NHCO(C_1$–$C_4$alkyl), or forms with $R_{26}$ a 5- or 6-membered ring optionally containing at least one heteroatom chosen from nitrogen, oxygen and sulphur;
- $R_{26}$ is chosen from a hydrogen atom; a halogen atom chosen from chlorine, bromine, iodine and fluorine; a $C_1$–$C_4$ alkyl radical; and a $C_1$–$C_4$ alkoxy radical, or forms with $R_{27}$ or $R_{28}$ a 5- or 6-membered ring optionally containing at least one heteroatom chosen from nitrogen, oxygen or sulphur;
- $R_{27}$ is chosen from a hydrogen atom, an —OH radical, an —$NHR_{28}$ radical, and an —$NR_{29}R_{30}$ radical;
- $R_{28}$ is chosen from a hydrogen atom, a $C_1$–$C_4$ alkyl radical, a $C_1$–$C_4$ monohydroxyalkyl radical, a $C_2$–$C_4$ polyhydroxyalkyl radical, and a phenyl radical;
- $R_{29}$ and $R_{30}$, which are identical or different, are chosen from a $C_1$–$C_4$ alkyl radical, a $C_1$–$C_4$ monohydroxyalkyl radical, and a $C_2$–$C_4$ polyhydroxyalkyl radical; and (b) a 5- or 6-membered nitrogen-containing heterocycle group which optionally contains additional heteroatoms, carbonyl-containing groups, or a mixture of additional heteroatoms and carbonyl-containing groups and which is unsubstituted or substituted with at least one radical chosen from $C_1$–$C_4$ alkyl, amino and phenyl radicals, and wherein said second composition comprises, in a medium suitable for dyeing, at least one oxidizing agent; and wherein either said first composition or said second composition further comprises at least one quaternary ammonium salt chosen from:

$(ii)_1$—quaternary ammonium salts of the following formula (V):

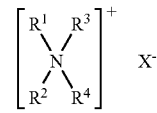

in which
the radicals $R^1$ $R^2$, $R^3$, and $R^4$, which are identical or different, are chosen from a saturated or unsaturated, linear or branched, aliphatic hydrocarbon radical comprising 1 to 30 carbon atoms; and a radical chosen from alkoxy, alkoxycarbonylalkyl, polyoxyalkylene, alkylamido, alkylamidoalkyl, hydroxyalkyl, aromatic, aryl and alkylaryl radicals comprising 12 to 30 carbon atoms, wherein at least one radical among $R^1$, $R^2$, $R^3$ and $R^4$ is a radical comprising 8 to 30 carbon atoms;

$X^-$ is an anion chosen from halides, phosphates, acetates, lactates and alkyl sulphates;

$(ii)_2$—imidazolium salts of the following formula (VI):

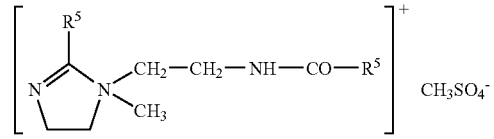

in which
$R^5$ is chosen from alkenyl radicals and alkyl radicals, said alkenyl radicals and alkyl radicals comprising 13 to 31 carbon atoms and being derived from tallow fatty acids;

$(ii)_3$—quaternary diammonium salts of the following formula (VII):

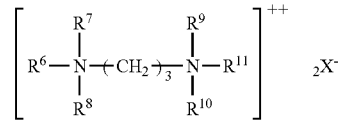

in which
$R^6$ is an aliphatic radical comprising 16 to 30 carbon atoms, $R^7$, $R^8$, $R^9$, $R^{10}$ and $R^{11}$ are chosen from hydrogen or an alkyl radical comprising 1 to 4 carbon atoms, and X is an anion chosen from halides, acetates, phosphates and sulphates.

* * * * *

UNITED STATES PATENT AND TRADEMARK OFFICE
CERTIFICATE OF CORRECTION

| | |
|---|---|
| PATENT NO. | : 7,198,652 B2 |
| APPLICATION NO. | : 11/384520 |
| DATED | : April 3, 2007 |
| INVENTOR(S) | : Christine Rondeau |

It is certified that error appears in the above-identified patent and that said Letters Patent is hereby corrected as shown below:

Claim 31, col. 62, line 57, delete "in which".

Claim 31, col. 63, line 1, insert --in which--.

Signed and Sealed this

Twenty-sixth Day of June, 2007

JON W. DUDAS
*Director of the United States Patent and Trademark Office*